(12) United States Patent
Silacci Melkko et al.

(10) Patent No.: US 11,351,267 B2
(45) Date of Patent: Jun. 7, 2022

(54) FGFR3 BINDING MOLECULES

(71) Applicant: Covagen AG, Zug (CH)

(72) Inventors: Michela Silacci Melkko, Zurich (CH); Richard Woods, Zurich (CH); Patricia Henne, London (GB); Barbara Zubler, Aurau (CH); Elena Kage, Dietikon (CH); Dragan Grabulovski, Zurich (CH); Julian Bertschinger, Ottenbach (CH)

(73) Assignee: Cilag GMBH International, Zug (CH)

( * ) Notice: Subject to any disclaimer, the term of this patent is extended or adjusted under 35 U.S.C. 154(b) by 107 days.

(21) Appl. No.: 16/901,160

(22) Filed: Jun. 15, 2020

(65) Prior Publication Data

US 2020/0345859 A1 Nov. 5, 2020

Related U.S. Application Data

(62) Division of application No. 15/943,137, filed on Apr. 2, 2018, now Pat. No. 10,722,589.

(30) Foreign Application Priority Data

Apr. 3, 2017 (EP) .................................. 17164482

(51) Int. Cl.
| | |
|---|---|
| *A61K 47/64* | (2017.01) |
| *C07K 16/28* | (2006.01) |
| *C07K 16/30* | (2006.01) |
| *C07K 19/00* | (2006.01) |
| *A61K 39/395* | (2006.01) |
| *A61K 39/00* | (2006.01) |
| *A61P 35/00* | (2006.01) |
| *C12N 9/12* | (2006.01) |

(52) U.S. Cl.
CPC ...... *A61K 47/6425* (2017.08); *A61K 47/6415* (2017.08); *A61P 35/00* (2018.01); *C07K 16/289* (2013.01); *C07K 16/2863* (2013.01); *C07K 16/2878* (2013.01); *C07K 16/2887* (2013.01); *C07K 16/30* (2013.01); *C07K 19/00* (2013.01); *C12N 9/12* (2013.01); *C12Y 207/10002* (2013.01); *A61K 39/39558* (2013.01); *A61K 2039/505* (2013.01); *C07K 2317/732* (2013.01); *C07K 2318/10* (2013.01); *C07K 2319/30* (2013.01); *C07K 2319/75* (2013.01)

(58) Field of Classification Search
CPC .............. A61K 47/64; A61K 39/39558; A61K 2039/505; C07K 16/2863; C07K 16/2878; C07K 19/00; C07K 16/2887; C07K 16/289; C07K 16/30
See application file for complete search history.

(56) References Cited

U.S. PATENT DOCUMENTS

| | | |
|---|---|---|
| 2005/0147612 A1 | 4/2005 | Yayon et al. |
| 2008/0044419 A1 | 2/2008 | Yayon |

FOREIGN PATENT DOCUMENTS

| | | |
|---|---|---|
| EP | 0 239 400 B1 | 8/1994 |
| EP | 2054432 B1 | 7/2015 |
| WO | WO 89/09622 A1 | 10/1989 |
| WO | WO 90/07861 A1 | 7/1990 |
| WO | WO 91/10741 A1 | 7/1991 |
| WO | WO 94/02602 A1 | 2/1994 |
| WO | WO 96/33735 A1 | 10/1996 |
| WO | WO 96/34096 A1 | 10/1996 |
| WO | WO 2006/048877 A2 | 5/2006 |
| WO | WO 2007/144893 A2 | 12/2007 |
| WO | WO 2008/022759 A2 | 2/2008 |
| WO | WO 2010/002862 A2 | 1/2010 |

(Continued)

OTHER PUBLICATIONS

Trudel et al., "The inhibitory anti-FGFR3 antibody, PRO-001, is cytotoxic to t(4;14) multiple myeloma cells", Blood, (2006) 107(10): 4039-4046.

Gebauer and Skerra, "Engineered protein scaffolds as next-generation antibody therapeutics", (2009) Curr Opinion in Chemical Biology 13:245-255.

(Continued)

*Primary Examiner* — Ruixiang Li
(74) *Attorney, Agent, or Firm* — Brian C. Carey

(57) ABSTRACT

The present invention relates to a polypeptide binding to fibroblast growth factor receptor 3 isoforms 3b and 3c (FGFR3b and FGFR3c), wherein the polypeptide comprises an amino acid sequence selected from the group consisting of: (a) GVTLFVALYDYEVYGPTPMLSFHKGEKFQIL $(X^1)(X^2)(X^3)$ $(X^4)$GPYWEARSL$(X^5)$TGETG$(X^6)$IPSNY-VAPVDSIQ (SEQ ID NO: 1), wherein amino acid positions (X1) to ($X^6$) may be any amino acid sequence; (b) an amino acid sequence which is at least 95% identical to the amino acid sequence of (a), wherein the identity determination excludes amino acid positions ($X^1$) to ($X^6$) and provided that the amino acid sequence EVYGPTPM (SEQ ID NO: 2) in amino acid positions 12 to 19 of SEQ ID NO: 1 is conserved and the amino acids P and Y in amino acid positions 37 and 38 of SEQ ID NO: 1 are conserved; (c) GVTLFVALYDYEVMSTTALSFHKGEKF QILSQSPHGQYWEARSLTTGETG($X^6$)IPSNYVAPVD-SIQ (SEQ ID NO: 19), wherein the amino acid position ($X^6$) may be any amino acid; and (d) an amino acid sequence which is at least 95% identical to the amino acid sequence of (c), wherein the identity determination excludes amino acid position ($X^6$) and provided that the amino acid sequences EVMSTTA (SEQ ID NO: 20) in amino acid positions 12 to 18 of SEQ ID NO: 19 and SQSPH (SEQ ID NO: 21) in amino acid positions 31 to 35 of SEQ ID NO: 19 are conserved and the amino acids Q and Yin amino acid positions 37 and 38 of SEQ ID NO: 19 are conserved.

12 Claims, 10 Drawing Sheets

Figure 2:
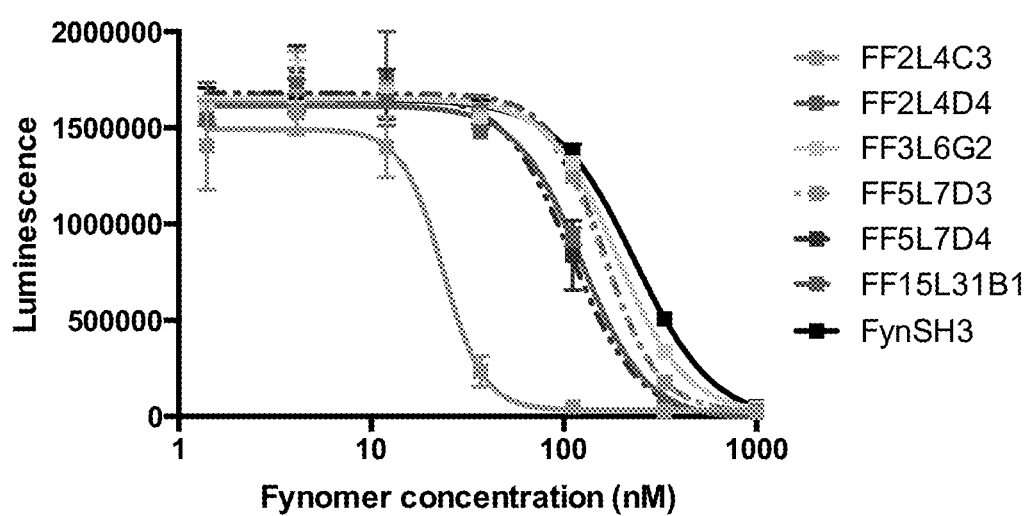

Specification includes a Sequence Listing.

(56) References Cited

FOREIGN PATENT DOCUMENTS

| WO | WO 2010/111367 A1 | 9/2010 |
|---|---|---|
| WO | WO 2011/023685 A1 | 3/2011 |
| WO | WO 2013/135588 A1 | 9/2013 |
| WO | WO 2014/044758 A1 | 3/2014 |
| WO | WO 2014/170063 A1 | 10/2014 |
| WO | WO 2015/141862 A1 | 9/2015 |

OTHER PUBLICATIONS

Kawakami et al., "Isolation and Oncogenic Potential of a Novel Human src-Like Gene", Molecular and Cellular Biology, vol. 6, No. 12 p. 4195-4201, (1986).
Altschul et al., "Gapped BLAST and PSI-BLAST: a new generation of protein database search programs", Nucleic Acids Res. 25:3389-3402 (1997).
Alberts et al., "Fusion Proteins Can Be Used to Analyze Protein Function and to Track Proteins in Living Cells", Molecular Biology of the Cell, $4^{th}$ ed. Garland Science, p. 518-519 2002.
Schier, "Efficient in vitro affinity maturation of phage antibodies using BIAcore guided selections", Human Antibodies Hybridomas vol. 7, 3 (1996), 97-105.
Malmborg et al., "BIAcore as a tool in antibody in engineering", J. Immunol. Methods 183 (1995), 7-13.
Strohl W. "Optimization of Fc-mediated effector functions of monoclonal antibodies", (2009) Curr Opin Biotechnol, 20, p. 685-691.
Johnson et al. Kabat database and it's applications:30 years after the first viability plot (2000) Nucleic Acids Res. 28, p. 214-218).
Braasch and Corey, "Locked nucleic acid (LNA): fine-tuning the recognition of DNA and RNA", Chemistry & Biology 8, 1-7 (2001). www.proteinatlas.org/ENSG00000068Q78-FGFR3/cancer).
Capellen et al., "Frequent activating mutations of FGFR3 in human bladder and cervic carcinomas", Nature Genetics (1999) vol. 23:18-20.
Lafitte et al., "FGFR3 has tumor suppressor properties in cells with epithelial phenotype", Molecular Cancer, (2013), vol. 12:83.
Sonvilla et al., "Fibroblast growth factor receptor 3-lllc mediates colorectal cancer growth and migration", British Journal of Cancer, (2010) 102(7):1145-1156).
Liao et al., "Inhibitor-Sensitive FGFR2 and FGFR3 Mutations in Lung Squamous Cell Carcinoma", (2013), Cancer Research, 73(16):5195-5205).
Turner, N. and R. Grose, „Fibroblast growth factor signalling: from development to cancer, Nat Rev Cancer, (2010) 10(2): p. 116-29.
Kalff, A. and A. Spencer, The t(4;14) translocation and FGFR3 overexpression in multiple myeloma: prognostic implications and current clinical strategies Blood Cancer J, (2012) vol. 2: p. e89.
Pollett, J.B., et al., "Overexpression of the myeloma-associated oncogene fibroblast growth factor receptor 3 confers dexamethasone resistance", Blood, (2002) 100(10): p. 3819-21.
Fonseca, R., et al., "Clinical and biologic implications of recurrent genomic aberrations in myeloma" Blood, (2003) 101(11): p. 4569-75.
Agazie, Y.M., et al., "The phosphotyrosine phosphatase SHP2 is a critical mediator of transformation induced by the oncogenic fibroblast growth factor receptor 3", Oncogene, (2003) 22(44): p. 6909-18.
Ronchetti, D., et al., "Deregulated FGFR3 mutants in multiple myeloma cell lines with t(4;14): comparative analysis of Y373C, K650E and the novel G384D mutations", Oncogene, (2001) 20(27): p. 3553-62.
Chesi, M., et al., "Activated fibroblast growth factor receptor 3 is an oncogene that contributes to tumor progression in multiple myeloma", Blood, (2001) 97(3): p. 729-36.
Plowright, E.E., et al., "Ectopic expression of fibroblast growth factor receptor 3 promotes myeloma cell proliferation and prevents apoptosis", Blood, (2000) 95(3): p. 992-8.
Chen, J., et al., Constitutively activated FGFR3 mutants signal through PLCgamma-dependent and -independent pathways for hematopoietic transformation, Blood, (2005) 106(1): p. 328-37.

Li, Z., et al., "The myeloma-associated oncogene fibroblast growth factor receptor 3 is transforming in hematopoietic cells", Blood, (2001) 97(8): p. 2413-9.
Trudel, S., et al., Inhibition of fibroblast growth factor receptor 3 induces differentiation and apoptosis in t(4;14) myeloma:, Blood, (2004) 103(9): p. 3521-8.
Trudel, S., et al., "CHIR-258, a novel, multitargeted tyrosine kinase inhibitor for the potential treatment of t(4;14) multiple myeloma", Blood, (2005) 105(7): p. 2941-8.
Chen, J., et al., "FGFR3 as a therapeutic target of the small molecule inhibitor PKC412 in hematopoietic malignancies. Oncogene", (2005) 24(56): p. 8259-67.
Paterson, J.L., et al., "Preclinical studies of fibroblast growth factor receptor 3 as a therapeutic target in multiple myeloma", Br J Haematol, (2004) 124(5): p. 595-603.
Grand, E.K., et al., "Targeting FGFR3 in multiple myeloma: inhibition of t(4;14)-positive cells by SU5402 and PD173074", Leukemia (2004) 18(5): p. 962-6.
Gomez-Roman, J.J., et al., "Fibroblast growth factor receptor 3 is overexpressed in urinary tract carcinomas and modulates the neoplastic cell growth", Clin Cancer Res, (2005) 11(2 Pt 1): p. 459-65.
Tomlinson, D.C., et al., "FGFR3 protein expression and its relationship to mutation status and prognostic variables in bladder cancer", J Pathology, (2007) 213(1): p. 91-8.
Van Rhijn, B.W., et al., Frequent FGFR3 mutations in urothelial papilloma:, J Pathology, (2002) 198(2): p. 245-51.
Tomlinson, et al., "Knockdown by shRNA identifies S249C mutant FGFR3 as a potential therapeutic target in bladder cancer", Oncogene, (2007) 26(40): p. 5889-99.
Martinez-Torrecuadrada, J., et al., "Targeting the extracellular domain of fibroblast growth factor receptor 3 with human single-chain Fv antibodies inhibits bladder carcinoma cell line proliferation", Clin Cancer Res, (2005) 11(17): p. 6280-90.
Martinez-Torrecuadrada, J.L., et al., "Antitumor activity of fibroblast growth factor receptor 3-specific immuno toxins in a xenograft mouse model of bladder carcinoma is mediated by apoptosis", Mol Cancer Ther, (2008) 7(4): p. 862-73.
Rauchenberger, R., et al., "Human combinatorial Fab library yielding specific and functional antibodies against the human fibroblast growth factor receptor 3", J Biol Chem, (2003) 278(40): p. 38194-205.
Brack, S., et al., "A bispecific HER2-targeting FynomAb with superior antitumor activity and novel mode of action", Mol Cancer Ther, (2014) 13(8): p. 2030-9.
Silacci, M., et al., "Discovery and characterization of COVA322, a clinical-stage bispecific TNF/IL-17A inhibitor for the treatment of inflammatory diseases" MAbs, (2016) 8(1): p. 141-9.
Schlatter, D., et al., "Generation, characterization and structural data of chymase binding proteins based on the human Fyn kinase SH3 domain", MAbs, (2012) 4(4): p. 497-508.
Grabulovski, D., et al., "A novel, non-immunogenic Fyn SH3-derived binding protein with tumor vascular targeting properties", J Biol Chem, (2007) 282(5): p. 3196-204.
Bertschinger, J., D. et al., "Selection of single domain binding proteins by covalent DNA display", Protein Eng Des Sel, (2007) 20(2): p. 57-68.
Wang et al., "Screening a phage display library for a novel FGF8b-bnding peptide with anti-tumor effect on prostate cancer", Experimental Cell Research, vol. 319. No. 8, pp. 1156-1164 XP055405147 (2013).
Dunois-Lard et al., "Absence of FGFR3 mutations in urinary bladder tumors of rats and mice treated with N0butyl-N-(-4-hydroxybutyl) nitrosamine", Molecular Carcinogenesis, vol. 42, No. 3, pp. 142-149, XP055198881 (2005).
Zhou et al., "FGFR3b Extracellular Loop Mutation Lacks Tumorigenicity In Vivo but Collaborates with p53/pRB Deficiency to Induce High-grated Papillary Urothelial Carcimona", Scientific Reports, vol. 6, No. 1, p. 1-11 XP0550405140 (2016).
Zhang et al., "Constitutive activating mutation of the FGFR3b in oral squamous cell carcinomas", International Journal of Cancer, vol. 117, No. 1 pp. 166-168 XP055405150 (2005).

(56) References Cited

OTHER PUBLICATIONS

Harding et al., "Blockage of Nonhormonal Fibroblast Growth Factors by FP-1039 Inhibits Growth of Multiple Types of Cancer", Science Translational Medicine, vol. 5, No. 178, pp. 1-9 XP0550405145 (2013).
Bernard-Pierrot et al., "Oncogenic properties of the mutated forms of fibroblast growth factor receptor 3b", Carcinogenesis, vol. 27, No. 4, pp. 740-747, XP002445932, (2006).

FIG. 1

CLUSTAL O(1.2.4) multiple sequence alignment

```
3  GVTLFVALYDYEVYGPTPMLSFHKGEKFQILNSSEGPYWEARSLTTGETGLIPSNYVAPVDSIQ
7  GVTLFVALYDYEVYGPTPMLSFHKGEKFQILRKGKGPYWEARSLATGETGLIPSNYVAPVDSIQ
4  GVTLFVALYDYEVYGPTPMLSFHKGEKFQILRGGQGPYWEARSLTTGETGLIPSNYVAPVDSIQ
5  GVTLFVALYDYEVYGPTPMLSFHKGEKFQILRGGDGPYWEARSLTTGETGLIPSNYVAPVDSIQ
6  GVTLFVALYDYEVYGPTPMLSFHKGEKFQILKGGSGPYWEARSLTTGETGLIPSNYVAPVDSIQ
8  GVTLFVALYDYEVYGPTPMLSFHKGEKFQILRRGSGPYWEARSLTTGETGLIPSNYVAPVDSIQ
   ************************************:..  .*********:*********
```

FIG. 3
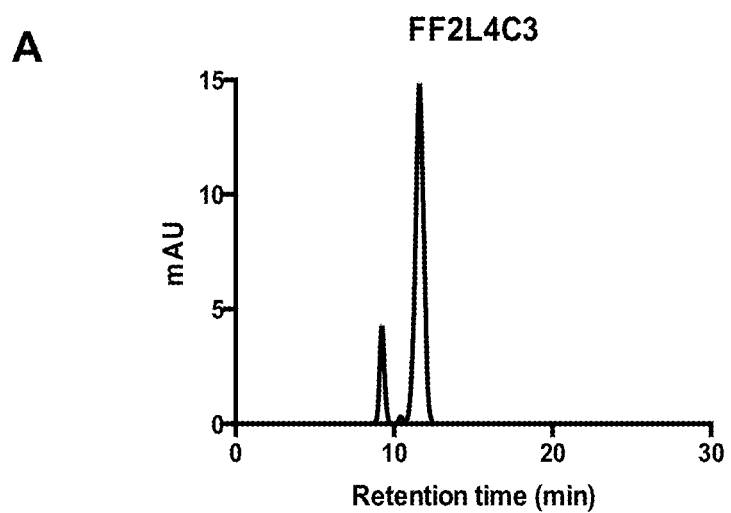
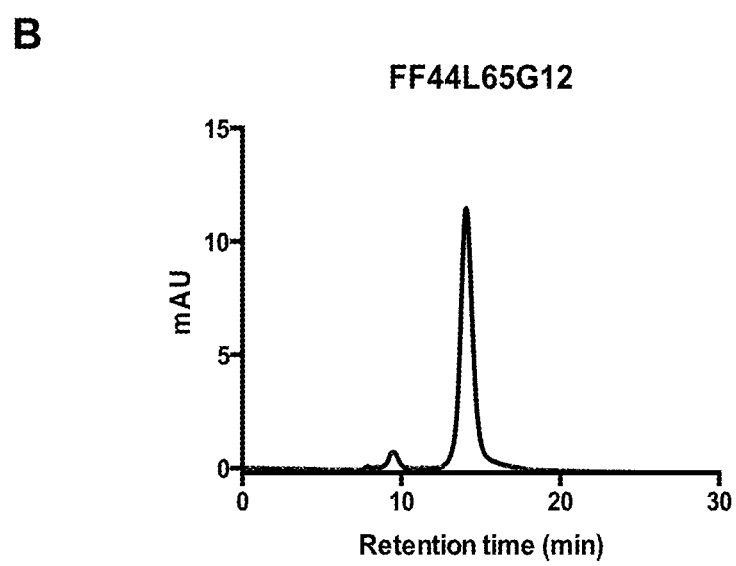

FIG. 3 CONT'D
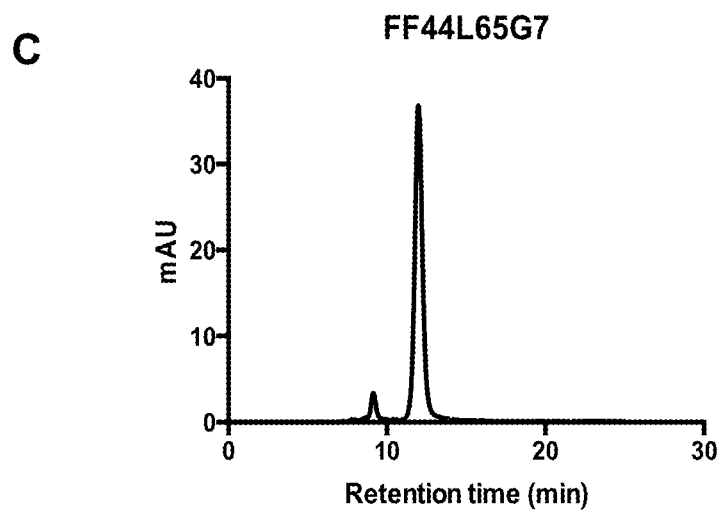
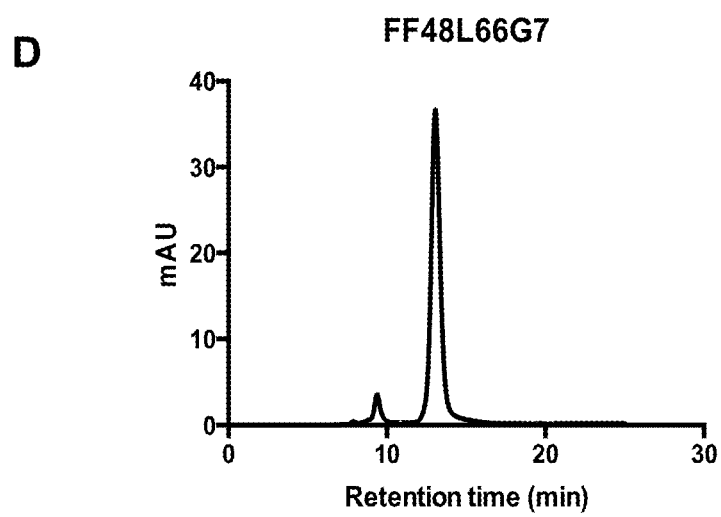

FIG. 3 CONT'D
E
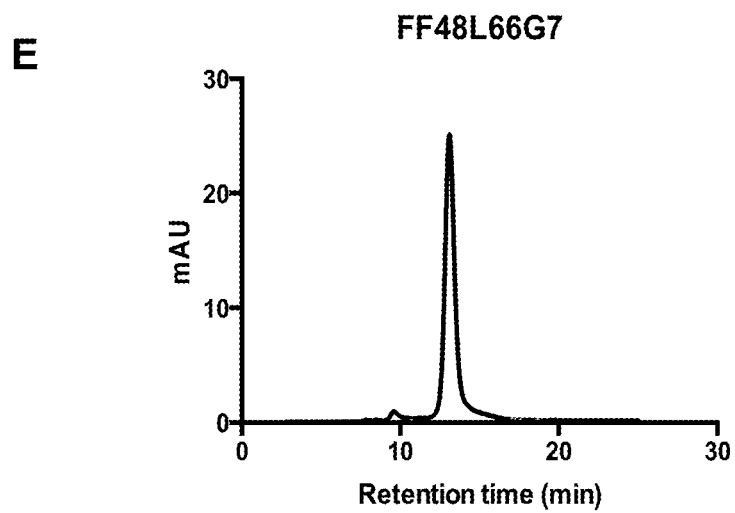
F
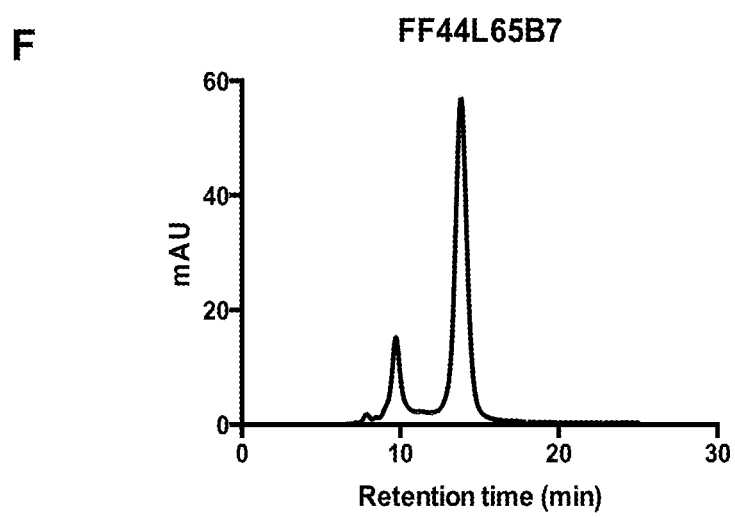

FIG. 4
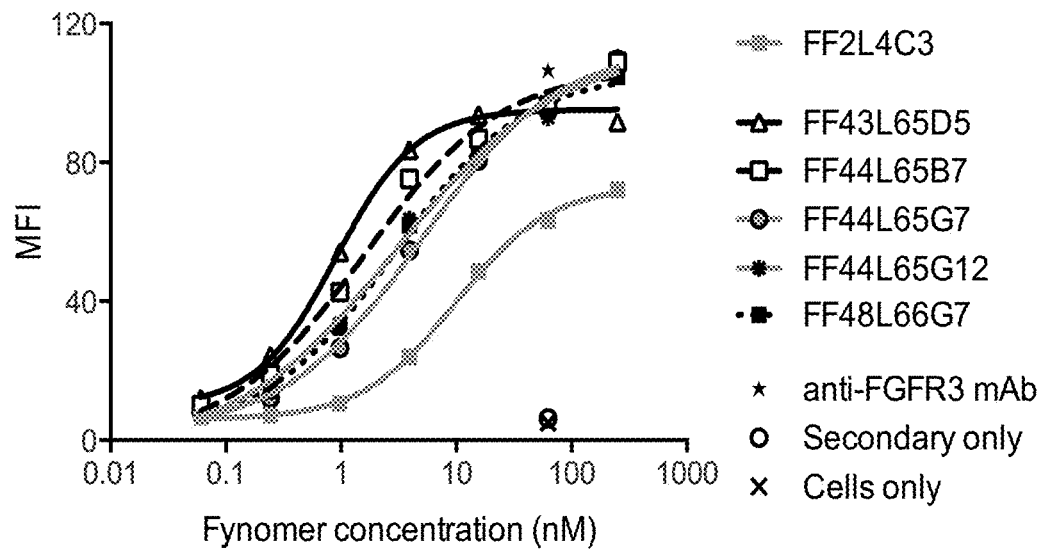
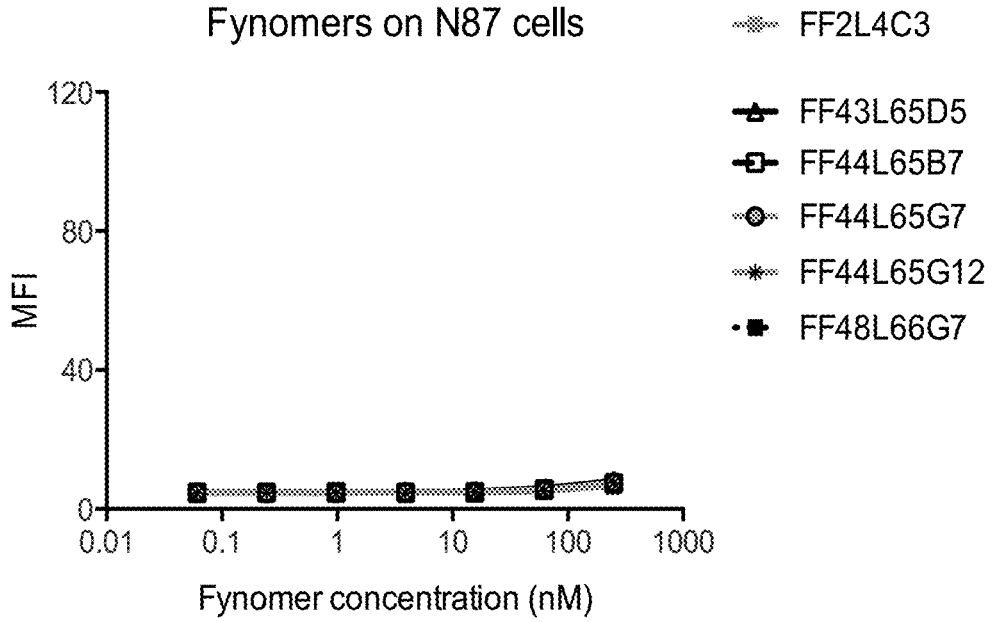

FIG. 5
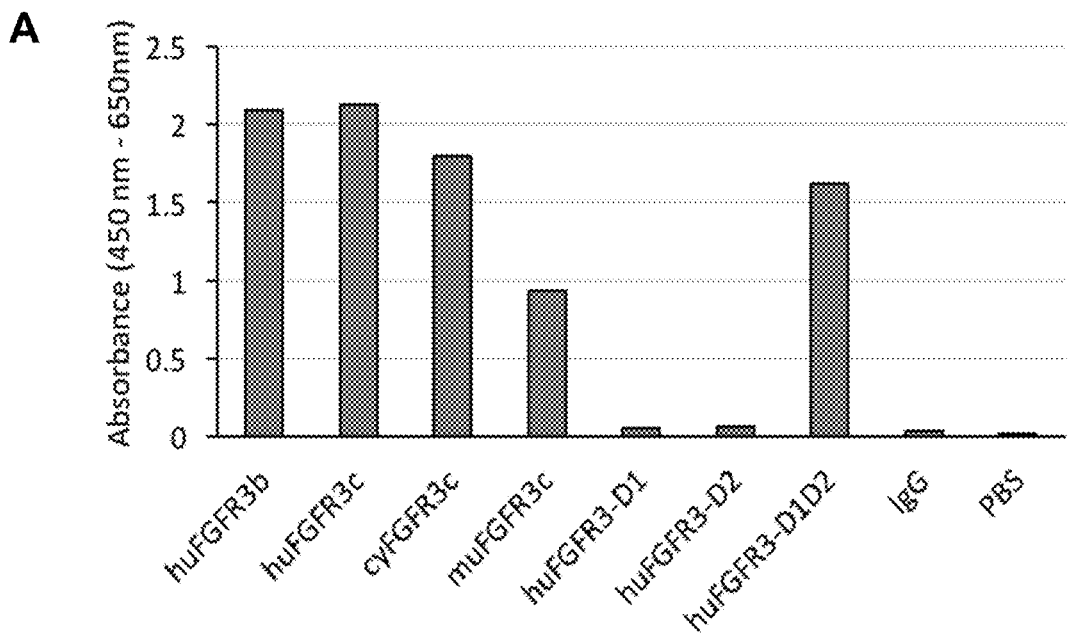
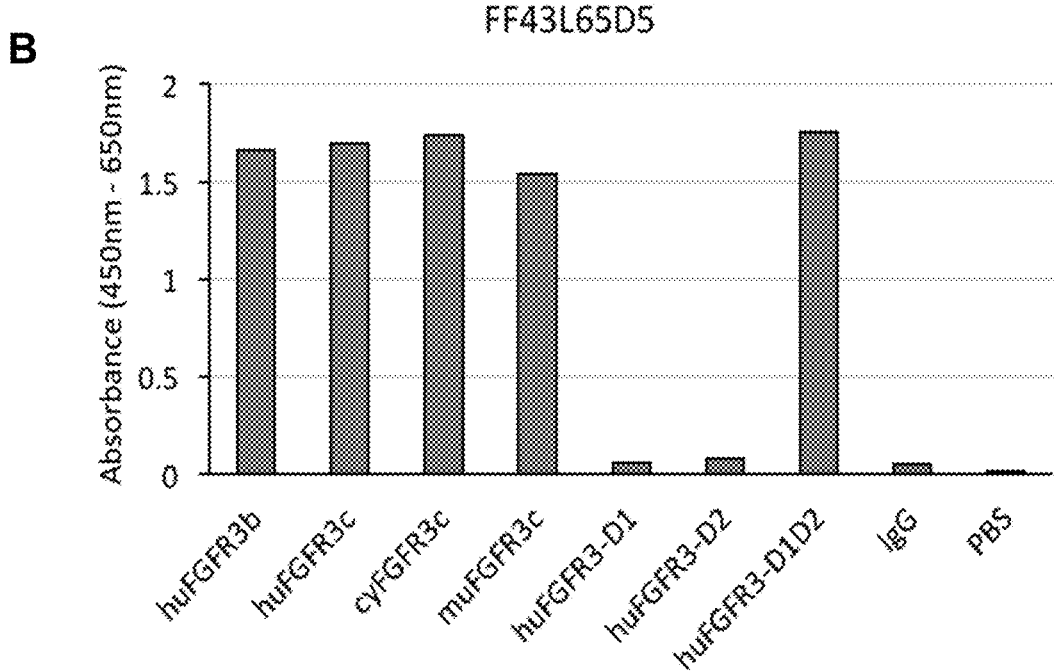

FIG. 5 CONT'D
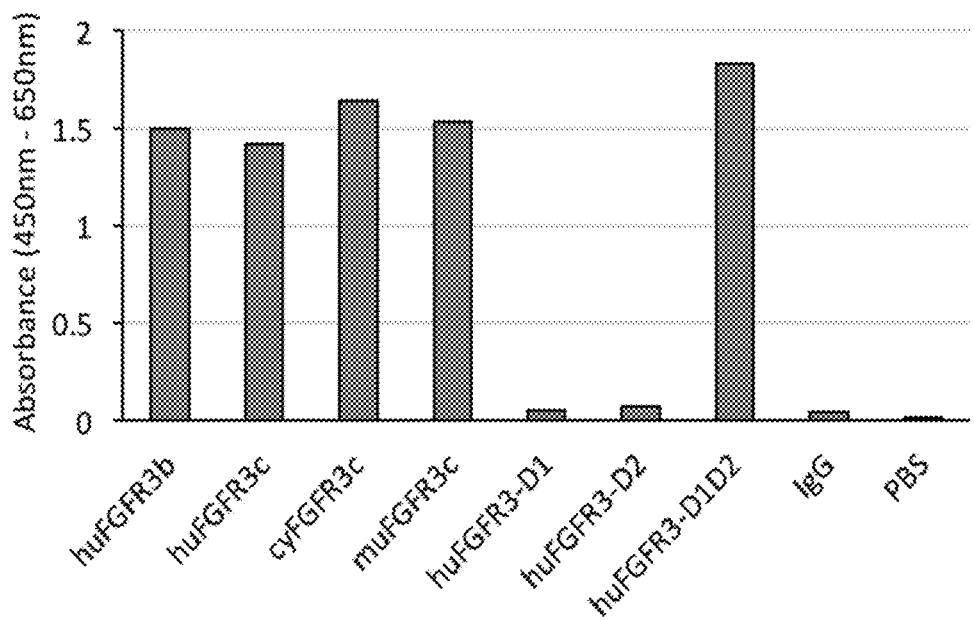
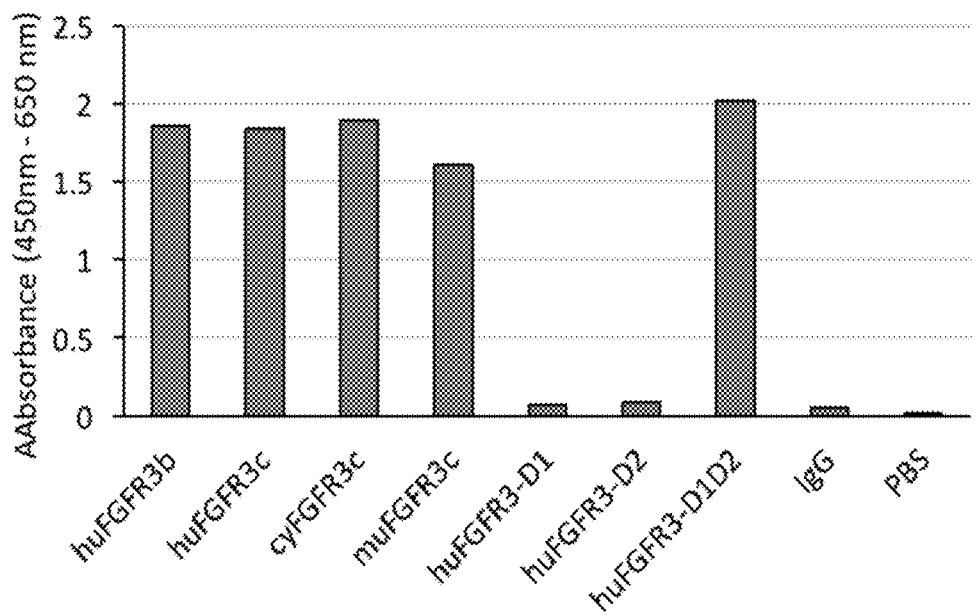

FIG. 5 CONT'D
E
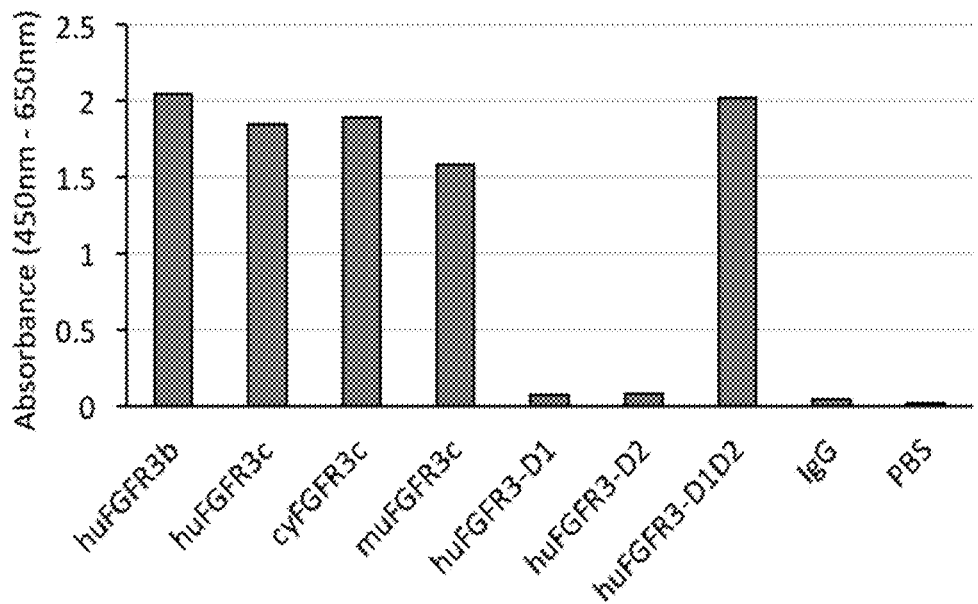
F
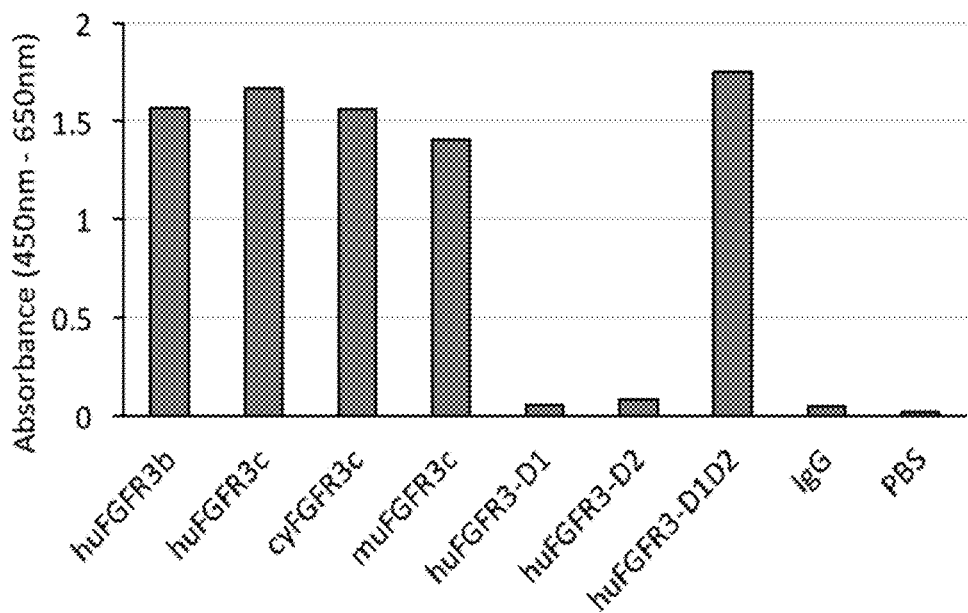

FIG. 6
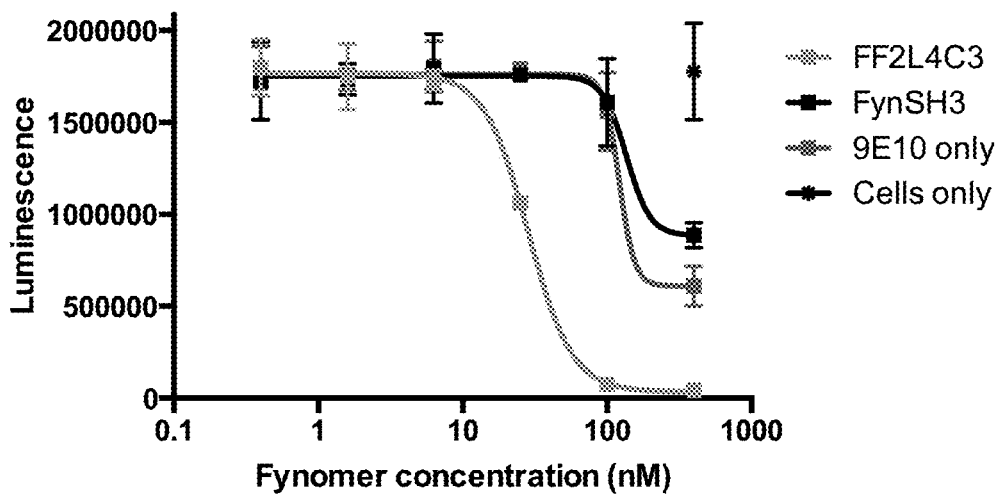
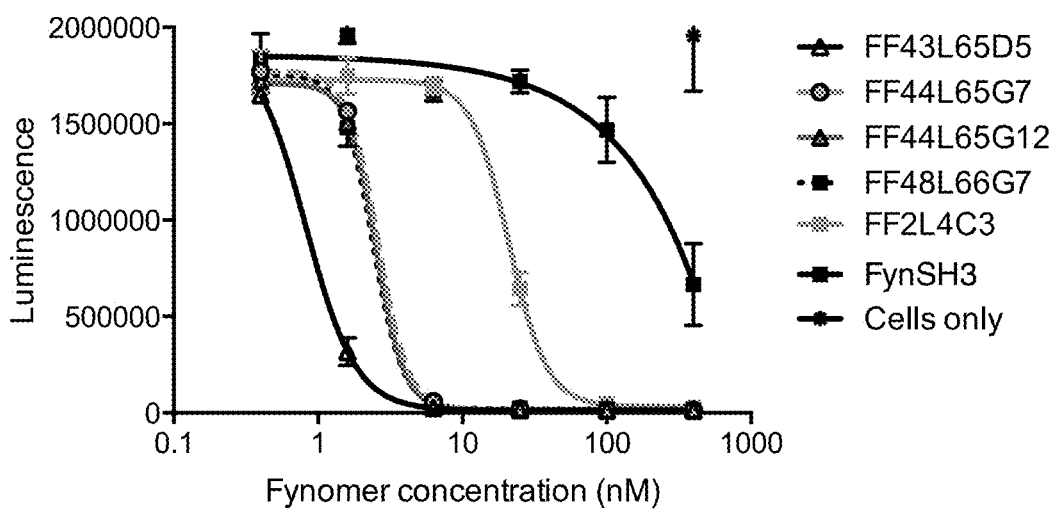
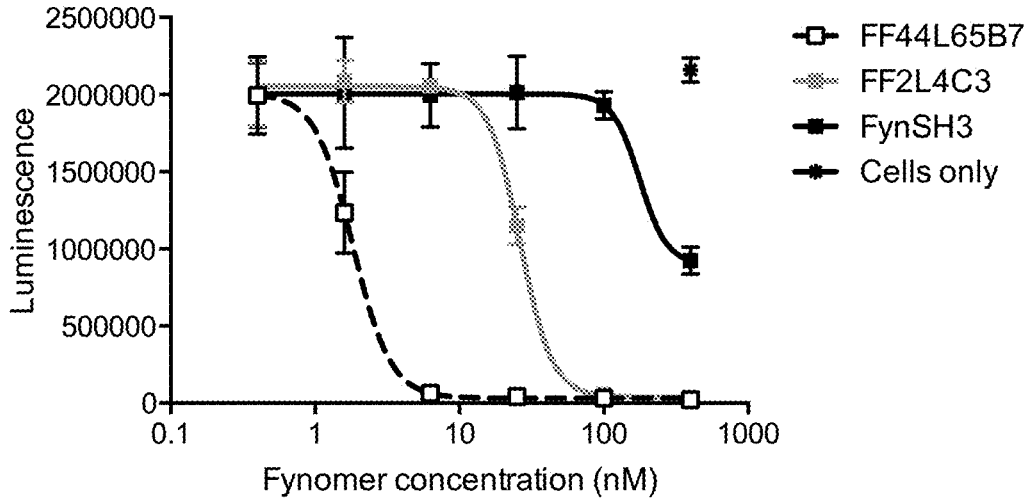

FGFR3 BINDING MOLECULES

This application is a divisional application of U.S. Ser. No. 15/943,137, filed Apr. 2, 2018, currently allowed, which claims priority from European patent application number EP 17164482.6, filed Apr. 3, 2017, the contents of which are hereby incorporated by reference in their entirety.

REFERENCE TO SEQUENCE LISTING SUBMITTED ELECTRONICALLY

This application contains a sequence listing, which is submitted electronically via EFS-Web as an ASCII formatted sequence listing with a file name "COV5008USDIV1SeqListing.txt", creation date of Apr. 13, 2020 and having a size of 41kb. The sequence listing submitted via EFS-Web is part of the specification and is herein incorporated by reference in its entirety.

BACKGROUND OF THE INVENTION

FGFR3 is one of four members of the FGFR family of transmembrane tyrosine kinase receptors that are involved in the intracellular signaling pathways. Activation of FGFR through interaction with fibroblast growth factors (FGFs) has been shown to have a critical role in both embryogenesis and adults with a pleiotropic range of sequelae, including cell proliferation and survival, migration, differentiation and growth arrest [1].

FGFRs consist of an extracellular ligand binding region, with two or three immunoglobulin-like domains (IgD1-3), a single-pass transmembrane region, and a cytoplasmic, split tyrosine kinase domain.

In humans, signaling is mediated by 1 of 22 FGF ligands, and ligand receptor specificity is controlled by differential cellular expression of the receptors, secretion of cell-surface proteins that modulate the interaction and alternative splicing of the receptors [1]. FGFR1, 2 and 3 each have two major alternatively spliced isoforms, designated IIIb and IIIc. These isoforms differ by about 50 amino acids in the second half of IgD3, and have distinct tissue distribution and ligand specificity. FGF ligands cause dimerization of FGFRs, which leads to activation and phosphorylation of the intracellular tyrosine kinase domain. This leads to activation of the several key pathways implicated in oncogenic signaling, including the mitogen-activated protein kinase (MAPK) and PI3K-AKT pathways.

Aberrantly activated FGFRs have been implicated in specific human malignancies [2]. In particular, the t(4;14) (p16.3;q32) chromosomal translocation occurs in about 15-20% of multiple myeloma patients, leading to overexpression of FGFR3 and correlates with shorter overall survival [2]. FGFR3 is implicated also in conferring chemoresistance to myeloma cell lines in culture [3], consistent with the poor clinical response of t(4;14) patients to conventional chemotherapy [4]. Overexpression of mutationally activated FGFR3 is sufficient to induce oncogenic transformation in hematopoietic cells and fibroblasts [5-8], transgenic mouse models [9], and murine bone marrow transplantation models [9, 10].

Accordingly, FGFR3 has been proposed as a potential therapeutic target in multiple myeloma. Indeed, several small-molecule inhibitors targeting FGFRs, although not selective for FGFR3 and having cross-inhibitory activity toward certain other kinases, have demonstrated cytotoxicity against FGFR3-positive myeloma cells in culture and in mouse models [11-15].

FGFR3 overexpression has been documented also in a high fraction of bladder cancers [16, 17]. Furthermore, somatic activating mutations in FGFR3 have been identified in 60-70% of papillary and 16-20% of muscle-invasive bladder carcinomas [17, 18]. In cell culture experiments, RNA interference [19] or an FGFR3 single-chain Fv antibody fragment inhibited bladder cancer cell proliferation [20]. A recent study demonstrated that an FGFR3 antibody-toxin conjugate attenuates xenograft growth of a bladder cancer cell line through FGFR3-mediated toxin delivery into tumors [21]. Publications relating to FGFR3 and anti-FGFR3 antibodies include US 2005/0147612; WO 2010/111367; Rauchenberger et al, J Biol Chem 278 (40):38194-38205 (2003)[22]; WO 2006/048877; Martinez-Torrecuadrada et al, (2008) Mol Cancer Ther 7(4): 862-873; WO 2007/144893; Trudel et al. (2006) 107(10): 4039-4046; Martinez-Torrecuadrada et al (2005) Clin Cancer Res 11 (17): 6280-6290; Gomez-Roman et al (2005) Clin Cancer Res 11:459-465; and WO 2010/002862.

These antibodies have one or more of the following disadvantages: they have the capability to recognize only one of the isoforms, or display a significant difference between affinities for the different isoforms.

Thus, there remains a need for molecules that can bind both splice variants FGFR3b and FGFR3c, with high affinity and specificity, and that are at the same time capable of being well internalized into a cell.

This need is addressed by the present invention.

DESCRIPTION OF THE INVENTION

From several different screens, a set of Fynomer polypeptides with a surprising mix of properties, including high affinity for both FGFR3b and FGFR3c and the capability for good internalization into cells, which set of polypeptides outperformed a large number of other candidates for a combination of these properties, was identified. The sequences of these polypeptides are disclosed herein. Apart from the polypeptides themselves, the invention also provides fusion constructs comprising such polypeptides, including fusions thereof to antibodies. The invention further provides nucleic acid molecules encoding polypeptides or fusion constructs of the invention. Further, pharmaceutical or diagnostic compositions comprising polypeptides or fusion constructs of the invention are provided, as well as such pharmaceutical compositions for use in treatment of cancer or T-cell mediated diseases.

The present invention relates in a first aspect to a polypeptide binding to fibroblast growth factor receptor 3 isoforms 3b and 3c (FGFR3b and FGFR3c), wherein the polypeptide comprises an amino acid sequence selected from the group consist.

(a)
(SEQ ID NO: 1)
GVTLFVALYDYEVYGPTPMLSFHKGEKFQIL($X^1$) ($X^2$) ($X^3$) ($X^4$) GPY

WEARSL($X^5$) TGETG($X^6$) IPSNYVAPVDSIQ, wherein amino acid positions ($X^1$) to ($X^6$) may be any amino acid sequence; (b) an amino acid sequence which is at least 95% identical to the amino acid sequence of (a), wherein the identity determination excludes amino acid positions ($X^1$) to ($X^6$) and provided that the amino acid sequence EVYGPTPM (SEQ ID NO: 2) in amino acid positions 12 to 19 of SEQ ID NO: 1 is conserved and the amino acids P and Y in amino acid positions 37 and 38 of SEQ ID NO: 1 are conserved;

(c)
(SEQ ID NO: 19)
GVTLFVALYDYEVMSTTALSFHKGEKFQILSQSPHGQYWEARSLTTGETG (X⁶)IPSNYVAPVDSIQ, wherein the amino acid position (X⁶) may be any amino acid; and (d) an amino acid sequence which is at least 95% identical to the amino acid sequence of (c), wherein the identity determination excludes amino acid position (X⁶) and provided that the amino acid sequences EVMSTTA (SEQ ID NO: 20) in amino acid positions 12 to 18 of SEQ ID NO: 19 and SQSPH (SEQ ID NO: 21) in amino acid positions 31 to 35 of SEQ ID NO: 19 are conserved and the amino acids Q and Y in amino acid positions 37 and 38 of SEQ ID NO: 19 are conserved.

The term "polypeptide" as used herein describes linear molecular chains of amino acids, including single chain proteins or their fragments, containing more than about 60 amino acids. Polypeptides may further form multimers, e.g. oligomers, consisting of at least two identical or different molecules. The corresponding higher order structures of such multimers are, correspondingly, termed homo- or heterodimers, homo- or heterotrimers etc. Furthermore, peptidomimetics of such polypeptides where amino acid(s) and/or peptide bond(s) have been replaced by functional analogs are also encompassed by the invention. Such functional analogues include all known amino acids other than the 20 gene-encoded amino acids, such as selenocysteine. The term "polypeptide" also refers to naturally modified polypeptides where the modification is effected e.g. by glycosylation, acetylation, phosphorylation and similar modifications which are well known in the art.

The polypeptide of the present invention is a Fyn SH3-derived polypeptide or Fynomer. Fyn SH3-derived polypeptides or Fynomers are well known in the art and have been described e.g. in Grabulovski et al. (2007) JBC, 282, p. 3196-3204; WO 2008/022759; Bertschinger et al (2007) Protein Eng Des Sel 20(2):57-68; and Gebauer and Skerra (2009) Curr Opinion in Chemical Biology 13:245-255. The term "Fyn SH3-derived polypeptide", used interchangeably herein with the term "Fynomer", refers to a non-immunoglobulin-derived binding polypeptide (e.g. a so-called scaffold as described in Gebauer and Skerra (2009) Curr Opinion in Chemical Biology 13:245-255) derived from the human Fyn SH3 domain. Fynomers are small about 7-kDa globular polypeptides. The SH3 domain of the human Fyn kinase was successfully used as a scaffold to engineer proteins (Fyn SH3-derived binding proteins termed Fynomers) that bind with high affinity and specificity to different target proteins (WO 2008/022759, WO 2011/023685, WO 2013/135588, WO 2014/170063, Grabulovski D. et al., (2007) J Biol Chem 282, p. 3196-3204, Bertschinger J. et al. (2007) Protein Eng Des Sel, 20, p. 57-68, and Schlatter et al. (2012) mAbs, 4(4) p. 497-50).

The phrase "binding to fibroblast growth factor receptor 3 isoforms 3b and 3c" (FGFR3b and FGFR3c or FGFR3b and 3c) as used requires that the polypeptides of the invention form binding interactions (in vivo and/or in vitro) with FGFR3b and FGFR3c. The isoforms 3b (FGFR3b) and 3c (FGFR3c) are formed by alternative splicing. The splice variants are generated by the use of two alternative exons, 3b and 3c, encoding the C-terminal half of the Ig domain 3. Epithelial cells show exclusively the 3b transcripts, while fibroblastic cells show a mixture of 3b and 3c transcripts. The amino acid sequence of human FGFR3b is shown in SEQ ID NO: 9 and the amino acid sequence of human FGFR3c is shown in SEQ ID NO: 10. The polypeptides of the invention preferably bind to the human fibroblast growth factor receptor 3 isoforms 3b and 3c. Preferably, the polypeptides of the invention bind to both isoforms, FGFR3b and FGFR3c with a $K_D$ of $10^{-7}$ to $10^{-12}$ M, more preferably $10^{-8}$ to $10^{-12}$ M, most preferably $10^{-9}$ to $10^{-12}$ M. In this regard it is preferred that the polypeptides of the invention specifically bind to FGFR3, preferably specifically to both isoforms FGFR3b and FGFR3c and thus do not significantly bind to other related proteins such as FGFR1, FGFR2, or FGFR4. In this respect significant binding preferably designates binding with a $K_D$ of $>5\times10^{-6}$ M.

SEQ ID NO: 1 and SEQ ID NO: 19 as shown herein above are derived from the amino acid sequence of the SH3 domain of the human Fyn kinase (SEQ ID NO: 11; aa 83-145 of Fyn kinase as reported by Kawakami et al. and Semba et al. in 1986). SEQ ID NO: 11 reads:

(SEQ ID NO: 11)
GVTLFVALYDY<u>EARTE</u>DDLSFHKGEKFQIL<u><u>NSSE</u></u>GDWWEARSLTTGETGY

IPSNYVAPVDSIQ.

In SEQ ID NO: 11 as shown above the sequences of the RT and the src loop are underlined and double-underlined, respectively. Grabulovski et al. (2007) JBC, 282, p. 3196-3204 investigated the influence of mutations in the RT and src loops of Fyn SH3 domains and demonstrated that mutations in these loops which are adjacent to the hydrophobic surface could determine the ability of this domain to participate in intermolecular associations. Moreover, EP 2054432 shows that mutations in and adjacent to the RT and/or the src loop determine the binding specificity of an SH3 domain. The amino acid sequence of the Fyn SH3 domain is fully conserved among man, mouse, rat and monkey (gibbon). Chicken Fyn SH3 differs in one, the one of Xenopus laevis in two amino acid positions from the corresponding human domain. Just as other SH3 domains the Fyn SH3 domain is composed of two antiparallel β-sheets and contains two flexible loops (called RT and src-loops) in order to interact with other proteins.

In more detail, SEQ ID NO: 1 is a sequence resulting from an alignment of SEQ ID NOs 3 to 8 (see FIG. 1). As it is evident from FIG. 1, positions ($X^1$) to ($X^4$) of SEQ ID NO: 1 correspond to the src-loop of the Fyn Kinase SH3 domain of SEQ ID NO: 11. Among SEQ ID NOs 3 to 8 the amino acids within the src-loop differ from each other. On the other hand, the second and third position C-terminally to the src-loop are "DW" in the wild-type sequence whereas the corresponding amino acids in all of SEQ ID NOs 3 to 8 are "PY". As it is furthermore evident from FIG. 1, the positions corresponding to the RT-loop of the Fyn Kinase SH3 domain of SEQ ID NO: 11 (i.e. the underlined sequence and the adjacent D), are changed as compared to the wild-type Fyn SH3 sequence but are conserved among SEQ ID NOs: 3 to 8 and have the sequence "EVYGPTPM" (SEQ ID NO: 2). The amino acid positions within the RT and src-loop including the amino acids being adjacent to these loops determine the binding specificity to FGFR3b and 3c.

In accordance with SEQ ID NO: 1 not only amino acid positions ($X^1$) to ($X^4$) may be any amino acid but also amino acid positions ($X^5$) and ($X^6$). As can be taken from FIG. 1, the amino acids in positions ($X^5$) and ($X^6$) may differ among SEQ ID NOs 3 to 8 or from the wild-type Fyn SH3 domain of SEQ ID NO: 11. It is believed that amino acids differences in these positions are not essential to the binding specificity of SEQ ID NOs 3 to 8. Thus, amino acid positions ($X^5$) and ($X^6$) may be exchanged or deleted, or further amino acids may be added, without substantially interfering with the binding specificity to FGFR3b and 3c. If amino acids are exchanged as compared to the amino acids that can be found in SEQ ID NOs 1 to 8 in amino acid positions ($X^5$) to ($X^6$), conservative exchanges are preferred.

SEQ ID NO: 19 is a sequence resulting from the anti-FGFR3b and FGFR3c polypeptide of SEQ ID NO: 22. Amino acid positions 12 to 18 of SEQ ID NO: 22 (EVMSTTA (SEQ ID NO: 20)) correspond to the RT-loop of the Fyn Kinase SH3 domain of SEQ ID NO: 11, and amino acid positions 31 to 35 of SEQ ID NO: 22 (SQSPH (SEQ ID NO: 21)) correspond to the src-loop of the Fyn Kinase SH3 domain of SEQ ID NO: 11. The second and third position C-terminally to the src-loop are "DW" in the wild-type sequence whereas the corresponding amino acids in SEQ ID NO: 22 are "QY". Also in SEQ ID NO: 22 the amino acid positions within the RT and src-loop including the amino acids being adjacent to these loops determine the binding specificity to FGFR3b and 3c.

In accordance with SEQ ID NO: 19 amino acid position ($X^6$) may be any amino acid. Amino acid position ($X^6$) of SEQ ID NO: 19 corresponds to amino acid position ($X^6$) of SEQ ID NO: 1. In SEQ ID NOs 1 and 19 amino acid ($X^6$) differs from the wild-type Fyn SH3 domain of SEQ ID NO: 11. The corresponding amino acid is Y in SEQ ID NO: 11, W in SEQ ID NO: 19 and L in SEQ ID NOs 3 to 8.

In accordance with the present invention, the term "percent (%) sequence identity" describes the number of matches ("hits") of identical nucleotides/amino acids of two or more aligned nucleic acid or amino acid sequences as compared to the number of nucleotides or amino acid residues making up the overall length of the template nucleic acid or amino acid sequences. In other terms, using an alignment, for two or more sequences or subsequences the percentage of amino acid residues or nucleotides that are the same (e.g. 95%, 97% or 98% identity) may be determined, when the (sub)sequences are compared and aligned for maximum correspondence over a window of comparison, or over a designated region as measured using a sequence comparison algorithm as known in the art, or when manually aligned and visually inspected. The sequences which are compared to determine sequence identity may thus differ by substitution(s), addition(s) or deletion(s) of nucleotides or amino acids. This definition also applies to the complement of a test sequence.

The skilled person is also aware of suitable programs to align polypeptide sequences. The percentage sequence identity of polypeptide sequences can, for example, be determined with programmes as the above explained programmes CLUSTLAW, FASTA and BLAST. Preferably the BLAST programme is used, namely the NCBI BLAST algorithm (Stephen F. Altschul, Thomas L. Madden, Alejandro A. Schäffer, Jinghui Zhang, Zheng Zhang, Webb Miller, and David J. Lipman (1997), "Gapped BLAST and PSI-BLAST: a new generation of protein database search programs", Nucleic Acids Res. 25:3389-3402).

With regard to the sequence identity as recited in item (b) herein above, it is preferred that the sequence identity is at least at least 98%. In this respect it is of further note that the sequence identity of at least 95% as recited in item (b) allows for two amino acid changes whereas the preferred identity of at least 98% allows for only one amino acid change. Hence, item (b) as recited herein above also pertains to an amino acid sequence which differs by two amino acid changes and preferably by one amino acid change from the amino acid sequence of item (a) as recited herein above, wherein the amino acid change(s) can be found in the amino acid positions of SEQ ID NO: 1 other than ($X^1$) to ($X^6$), the amino acid sequence EVYGPTPM (SEQ ID NO: 2) in amino acid positions 12 to 19 of SEQ ID NO: 1, and the amino acids P and Y in amino acid positions 37 and 38 of SEQ ID NO: 1. It is believed that amino acids in SEQ ID NO: 1 other than ($X^1$) to ($X^6$), the amino acid sequence EVYGPTPM (SEQ ID NO: 2) in amino acid positions 12 to 19 of SEQ ID NO: 1, and the amino acids P and Y in amino acid positions 37 and 38 of SEQ ID NO: 1 are not essential to the binding specificity of SEQ ID NOs 3 to 8. Thus, these amino acids positions may be exchanged or deleted, or an amino acid may be added, without substantially interfering with the binding specificity to FGFR3b and 3c. These amino acid positions are preferably exchanged. If amino acids are exchanged, conservative exchanges are preferred.

With regard to the sequence identity as recited in item (d) herein above, it is preferred that the sequence identity is at least at least 97%. In this respect it is of further note that the sequence identity of at least 95% as recited in item (d) allows for two amino acid changes whereas the preferred identity of at least 97% allows for only one amino acid change. Hence, item (d) as recited herein above also pertains to an amino acid sequence which differs by two amino acid changes and preferably by one amino acid change from the amino acid sequence of item (c) as recited herein above, wherein the amino acid change(s) can be found in the amino acid positions of SEQ ID NO: 19 other than the amino acid sequences EVMSTTA (SEQ ID NO: 20) in amino acid positions 12 to 18 of SEQ ID NO: 19 and SQSPH (SEQ ID NO: 21) in amino acid positions 31 to 35 of SEQ ID NO: 19 and the amino acids Q and Y in amino acid positions 37 and 38 of SEQ ID NO: 19. It is believed that amino acids in SEQ ID NO: 19 other the amino acid sequences EVMSTTA (SEQ ID NO: 20) in amino acid positions 12 to 18 of SEQ ID NO: 19 and SQSPH (SEQ ID NO: 21) in amino acid positions 31 to 35 of SEQ ID NO: 19 and the amino acids Q and Y in amino acid positions 37 and 38 of SEQ ID NO: 19 are not essential to the binding specificity of SEQ ID NO: 22. Thus, these amino acids positions may be exchanged or deleted, or an amino acid may be added, without substantially interfering with the binding specificity to FGFR3b and 3c. These amino acid positions are preferably exchanged. If amino acids are exchanged, conservative exchanges are preferred.

The phrase "the identity determination excludes amino acid positions ($X^1$) to ($X^6$)" as used herein in connection with SEQ ID NO: 1 specifies that the calculation of the sequence identity with regard to SEQ ID NO: 1 does not take into account amino acid positions ($X^1$) to ($X^6$). Likewise, the phrase "the identity determination excludes amino acid position ($X^6$)" as used herein in connection with SEQ ID NO: 19 specifies that the calculation of the sequence identity with regard to SEQ ID NO: 19 does not take into account amino acid position ($X^6$).

The condition "provided that the amino acid sequence EVYGPTPM (SEQ ID NO: 2) in amino acid positions 12 to 19 of SEQ ID NO: 1 is conserved" as used herein specifies that no amino acids changes may be introduced into amino acid positions 12 to 19 of SEQ ID NO: 1. Likewise, the condition "provided that the amino acids P and Y in amino acid positions 37 and 38 of SEQ ID NO: 1 are conserved" as used herein specifies that no amino acid changes may be introduced into amino acid positions 37 and 38 of SEQ ID NO: 1. In other terms, the amino acid positions corresponding to amino acid positions 12 to 19 of SEQ ID NO: 1 have the sequence EVYGPTPM (SEQ ID NO: 2) and the amino acids in positions 37 and 38 are P and Y, respectively, in all polypeptides falling under the ambit of items (a) and (b) of the first embodiment of the invention and the preferred examples thereof.

The condition "provided that the amino acid sequences EVMSTTA (SEQ ID NO: 20) in amino acid positions 12 to 18 of SEQ ID NO: 19 and SQSPH (SEQ ID NO: 21) in amino acid positions 31 to 35 of SEQ ID NO: 19 are conserved" as used herein specifies that no amino acids changes may be introduced into amino acid positions 12 to 18 as well as 31 to 35 of SEQ ID NO: 19. Likewise, the condition "provided that the amino acids Q and Y in amino acid positions 37 and 38 of SEQ ID NO: 19 are conserved" as used herein specifies that no amino acid changes may be introduced into amino acid positions 37 and 38 of SEQ ID NO: 19. In other terms, the amino acid positions corresponding to amino acid positions 12 to 18 of SEQ ID NO: 19 have the sequence EVMSTTA (SEQ ID NO: 20), the amino acid positions corresponding to amino acid positions 31 to 35 of SEQ ID NO: 19 have the sequence SQSPH (SEQ ID NO: 21) and the amino acids in positions 37 and 38 are Q and Y, respectively, in all polypeptides falling under the ambit of items (c) and (d) of the first embodiment of the invention and the preferred examples thereof.

As mentioned, any amino acid substitution in SEQ ID NO: 1 and SEQ ID NO: 19 is preferably a conservative amino acid substitution. A conservative substitution specifies the replacement of an amino acid with another amino acid having a chemical property similar to the amino acid that is replaced. Preferably, the conservative substitution as referred to herein is a substitution selected from the group consisting of: (i) a substitution of a basic amino acid with a different basic amino acid; (ii) a substitution of an acidic amino acid with a different acidic amino acid; (iii) a substitution of an aromatic amino acid with a different aromatic amino acid; (iv) a substitution of a non-polar, aliphatic amino acid with a different non-polar, aliphatic amino acid; and (v) a substitution of a polar, uncharged amino acid with a different polar, uncharged amino acid. Basic amino acids are arginine, histidine, and lysine.

Acidic amino acids are aspartate and glutamate. Aromatic amino acids are phenylalanine, tyrosine and tryptophane. Non-polar, aliphatic amino acids are glycine, alanine, valine, leucine, methionine, isoleucine and proline. Polar, uncharged amino acids are serine, threonine, cysteine, asparagine and glutamine. In contrast to a conservative amino acid substitution, a non-conservative amino acid substitution is the exchange of one amino acid with any amino acid that does not fall under the above-outlined conservative substitutions (i) through (v).

The anti-FGFR3 Fynomers disclosed herein advantageously have an excellent binding affinity to FGFR3c and 3b and are furthermore particularly suitable for being internalized into cells, where they can exert a diagnostic or therapeutic effect. As can be taken from the examples herein below, the anti-FGFR3 Fynomer of SEQ ID NOs 3 was found when screening a large library of Fynomers. The anti-FGFR3 Fynomers of SEQ ID NOs 3 and 19 have been proven to have outstanding properties in terms of their binding affinity to the FGFR3 isoforms 3b and 3c as well as their cell internalization properties; see Examples 1 and 7. Hence, the Fynomer with SEQ ID NO: 19 is an alternative to the Fynomers of SEQ ID NO: 1. Unexpectedly and advantageously both Fynomers have a similar combination of advantageous properties. The anti-FGFR3 Fynomer of SEQ ID NO: 3 was used as a template for affinity maturation and it was even possible to further improve the binding affinity to FGFR3b and 3c. In more detail, among a large pool of polypeptides that resulted from the affinity maturation process, the anti-FGFR3 Fynomer of SEQ ID NO: 4 to 8 were found to even more strongly bind to FGFR3b and 3c than the anti-FGFR3 Fynomer of SEQ ID NO: 3. The examples herein below furthermore show that the anti-FGFR3 Fynomers of SEQ ID NOs 3 to 8 and 22 can be recombinantly produced and have favourable manufacturability properties, and hence can be produced in large scale, e.g., for therapeutic and diagnostic applications. In addition, the anti-FGFR3 Fynomers of SEQ ID NO: 3 to 8 and 22 not only bind to human FGFR3c and 3b but also to FGFR3c (and likely also 3b) of mouse and monkey. This cross-species binding is advantageous for preclinical tests. These molecules could be used for diagnostic purposes, and are also suitable as a starting point for development of further therapeutic agents against tumor cells that express FGFR3 on their surface, for instance as described in more detail herein. None of the other anti-FGFR3 Fynomers identified by the initial screenings or in the subsequent affinity maturation process had a similar advantageous combination of properties as the anti-FGFR3 Fynomers of SEQ ID NOs 3 to 8 and 22. The surprising and unpredictable advantageous combination of properties of the anti-FGFR3 Fynomers of SEQ ID NOs 3 to 8 and 22 will be further apparent from the examples herein below.

In accordance with a preferred embodiment of the first aspect of the invention, $(X^1)$ is N, R, or K, and is preferably R or K; $(X^2)$ is S, G, K or R, and is preferably G, K or R; $(X^3)$ is S or G, and is preferably G; and $(X^4)$ is E, Q, D, S or K, and is preferably Q, D, S or K.

In accordance with another preferred embodiment of the first aspect of the invention, $(X^1)$ is N, R, or K, and is preferably R or K; $(X^2)$ is S, G, K or R, and is preferably G, K or R; $(X^3)$ is S or G, and is preferably G; $(X^4)$ is E, Q, D, S or K, and is preferably Q, D, S or K; $(X^5)$ is T or A; and $(X^6)$ is Y, W or L, and is preferably L or W.

Amino acid positions $(X^1)$ to $(X^4)$ in SEQ ID NO: 1 are the amino acid positions corresponding to the amino acids forming the src-loop of the human wild-type Fyn SH3 domain. The examples herein below show that the amino acids listed for amino acid positions $(X^1)$ to $(X^4)$ confer binding specificity to FGFR3b and FGFR3c, in particular FGFR3b having SEQ ID NO: 9 and FGFR3c having SEQ ID NO: 10. In more detail, the sequence alignment of SEQ ID NOs 3 to 8 of the invention in FIG. 1 shows that in the anti-FGFR3 Fynomers of SEQ ID NOs 3 to 8 the amino acids can be found that are listed for amino acid positions $(X^1)$ to $(X^4)$ in the above preferred embodiment. The preferred amino acids that are listed for amino acid positions $(X^1)$ to $(X^4)$ in the above preferred embodiment can be found in the corresponding amino acid positions of SEQ ID NOs 4 to 8, noting that SEQ ID NOs 4 to 8 were obtained from SEQ ID NO: 3 by affinity maturation. It can be expected that also other amino acid sequences selected from $(X^1)$ to $(X^4)$ as defined above than the specific amino acid combinations for $(X^1)$ to $(X^4)$ as present in SEQ ID NOs 3 to 8, preferably in SEQ ID NOs 4 to 8 confer binding specificity to FGFR3b and 3c.

As discussed above, amino acid position $(X^5)$ in SEQ ID NO: 1 and amino acid position $(X^6)$ in SEQ ID NOs 1 and 19 are amino acid positions that neither correspond to the amino acids of the RT and src-loop of the human wild-type Fyn SH3 domain nor amino acids being adjacent to one of these loops. Hence, it is believed that the amino acids in these positions can be exchanged or deleted, or a further amino acid may be added, without substantially interfering with the binding specificity to FGFR3b and 3c. The amino acids in positions $(X^5)$ and $(X^6)$ are preferably exchanged. It is more preferred that $(X^5)$ is T or A; and $(X^6)$ is Y, W or L, and is most preferably L or W. As can be taken from FIG. 1 these amino acids for $(X^5)$ of SEQ ID NO: 1 and $(X^6)$ of SEQ ID NOs 1 and 19 can either be found in SEQ ID NOs 3 to 8 and 22 or the human Fyn SH3 wild-type domain (SEQ ID NO: 11) or in another FGFR3b and 3c binding Fynomer. In the case of the most preferred amino acid for position $(X^6)$ this amino acid can be found in SEQ ID NOs 3 to 8.

In accordance with a more preferred embodiment of the first aspect of the invention, the polypeptide comprises an amino acid sequence selected from the group consisting of any one of SEQ ID NOs 3 to 8 and 22, preferably from any one of SEQ ID NOs 4 to 8 or 22.

As can be taken from the examples herein below SEQ ID NOs 3 to 8 and 22 are the sequences of the concrete anti-FGFR3b and 3c Fynomers that were generated and tested.

In accordance with an even more preferred embodiment of the first aspect of the invention, the polypeptide comprises an amino acid sequence selected from the group consisting of: SEQ ID NO: 4, SEQ ID NO: 5, SEQ ID NO: 6, SEQ ID NO: 7, SEQ ID NO: 8, and SEQ ID NO: 22. A polypeptide comprising an amino acid sequence of SEQ ID NO: 6 is particularly preferred. Another particularly preferred embodiment is a polypeptide comprising an amino acid sequence of SEQ ID NO: 22.

It was quite surprising to obtain a Fynomer with low nanomolar affinity already in a first screen. A Fynomer having SEQ ID NO 3 was isolated from a library of Fynomers as the Fynomer having the most outstanding FGFR3b and 3c binding affinity and internalization properties. Fynomers with SEQ ID NOs 4 to 8 were derived from SEQ ID NO: 3, and the FGFR3b and 3c binding affinity of Fynomers having SEQ ID NOs 4 to 8 is even further improved.

Suprisingly a Fynomer with SEQ ID NO: 22 also had very good properties, comparable to those with SEQ ID NOs 4 to 8, although it was initially derived from a different family of Fynomers.

The present invention relates in a second aspect to a fusion construct comprising the polypeptide of the invention fused to a further compound.

A "fusion construct" has used herein defines the fusion of the polypeptide of the invention to a further compound. The compound may either be a proteinous compound or a non-proteinous compound. In the case the compound is a proteinous compound (e.g. a cytokine or chemokine, or an antibody or antibody fragment, as described herein below), the fusion construct may also be designated as fusion protein. The term "fusion protein" as used herein is in general terms directed to a polypeptide construct generated through the joining and expression of two or more genes which code for separate polypeptides or a polypeptide and a peptide. In other words, translation of this fusion gene results in a single polypeptide with functional properties derived from each of the original polypeptides. The polypeptides may either be directly fused or via a linker, i.e. a short peptide sequence. In general, fusion proteins are generated artificially by recombinant DNA technology well know to the skilled person (e.g. Alberts et al., Molecular Biology of the Cell, 4$^{th}$ ed. Garland Science, p. 518-519). However, polypeptides and fusion proteins of the invention may be prepared by any of the many conventional and well known techniques such as plain organic synthetic strategies, solid phase-assisted synthesis techniques or by commercially available automated synthesizers. Fusion proteins may be used in biological research, diagnostics or therapeutics.

Examples of non-proteinous compounds as the further compound are, for example, small organic molecules, such as polyethylenglycol (PEG) or Alexa Fluor, or radionuclides. Further specific examples of non-proteinous further compounds are discussed herein below.

In accordance with certain embodiments of the second aspect of the invention the further compound is a pharmaceutically active compound, a prodrug, a pharmaceutically acceptable carrier, a diagnostically active compound, a cell penetrating enhancer, and/or a compound modulating serum half-life.

A pharmaceutically active compound is a compound having a biological activity upon administration to a subject, which brings about a beneficial effect for the subject. A prodrug is a compound that is administered in an inactive (or less than fully active) form to a subject, and is subsequently converted to a pharmaceutically active or pharmaceutically fully active compound through metabolic processes in the subject. The pharmaceutically (fully) active compound is preferably a compound suitable for the treatment of prevention of any of the specific diseases defined herein below.

A diagnostically active compound is a compound having an activity upon administration to a subject, which allows (assisting in) determining or identifying a disease or disorder, if an individual is afflicted with. Examples of diagnostically active compounds include detectable markers such as fluorescent dyes, radionuclides or contrast agents for medical imaging. Specific examples of fluorescent dyes, radionuclides and contrast agents for medical imaging are described herein below. A diagnostically active compound fused to a polypeptide of the invention can in particular be used to assist in determining or identifying, or to determine or identify any one of the specific diseases defined herein below which have in common that their origin and/or symptom(s) are FGFR3-related, in particular FGFR3b and 3c-related. The sites of such disease within the body of a subject can be detected or identified by the polypeptide of the invention fused to the diagnostically active compound of the invention.

A cell penetrating enhancer is a compound facilitating the delivery of the polypeptide of the invention into a (in vitro, ex vivo or in vivo) cell.

A compound modulating serum half-life is a compound which allows for extending the in vivo half-life of the polypeptides of the invention, in particular in the blood circulation system. The component modulating serum half-life is preferably polyethylene glycol (PEG).

A pharmaceutically acceptable carrier is a compound that facilitates or improves, e.g., the delivery and/or the effectiveness of the polypeptide of the invention upon administration to a subject. Suitable pharmaceutically-acceptable carriers are well known in the art and include, for example, stabilizers, antioxidants, pH-regulating substances, etc.

In accordance with one embodiment of the second aspect of the invention, the further compound is a toxic compound.

The toxic compound is preferably a small organic compound or a polypeptide, for example a toxic compound selected from the group consisting of calicheamicin, maytansinoid, neocarzinostatin, esperamicin, dynemicin, kedarcidin, maduropeptin, doxorubicin, daunorubicin, auristatin, Ricin-A chain, modeccin, truncated *Pseudomonas* exotoxin A, diphtheria toxin and recombinant gelonin.

In accordance with another embodiment of the second aspect of the invention the further compound of the invention is selected from the group consisting of (a) a fluorescent dye, (b) a photosensitizer, (c) a radionuclide, (d) a contrast agent for medical imaging, (e) a cytokine, (f) a chemokine, (g) a pro-coagulant factor, (h) an enzyme for pro-drug activation, (i) an albumin binder, (j) an albumin, (k) an IgG binder, or (l) polyethylene glycol.

Examples of a fluorescent dye are Alexa Fluor and Cy dyes.

Examples of a photosensitizer are phototoxic red fluorescent protein KillerRed and haematoporphyrin.

Examples of a radionuclide are gamma-emitting isotopes, e.g. $^{99m}$Tc, $^{123}$I, $^{111}$In, positron emitters, e.g. $^{18}$F, $^{64}$Cu, $^{68}$Ga, $^{86}$Y, $^{124}$I, beta-emitters, e.g. $^{131}$I, $^{90}$Y, $^{177}$Lu, $^{67}$Cu, and alpha-emitters, e.g. $^{213}$Bi, $^{211}$At.

A contrast agent as used herein is a substance used to enhance the contrast of structures or fluids within the body in medical imaging. Common contrast agents work based on X-ray attenuation and magnetic resonance signal enhancement.

A cytokine can for instance be selected from the group consisting of IL-2, IL-12, TNF-alpha, IFN alpha, IFN beta, IFN gamma, IL-10, IL-15, IL-24, GM-CSF, IL-3, IL-4, IL-5, IL-6, IL-7, IL-9, IL-11, IL-13, LIF, CD80, B70, TNF beta, LT-beta, CD-40 ligand, Fas-ligand, TGF-beta, IL-1alpha and IL-1beta. As it is well-known in the art, cytokines may favour a pro-inflammatory or an anti-inflammatory response of the immune system. Thus, depending on the disease to be treated either fusion constructs with a pro-inflammatory or an anti-inflammatory cytokine may be favored. For example, for the treatment of inflammatory diseases in general fusion constructs comprising anti-inflammatory cytokines are preferred, whereas for the treatment of cancer in general fusion constructs comprising pro-inflammatory cytokines are preferred.

A chemokine can for instance be selected from the group consisting of IL-8, GRO alpha, GRO beta, GRO gamma, ENA-78, LDGF-PBP, GCP-2, PF4, Mig, IP-10, SDF-1alpha/beta, BUNZO/STRC33, I-TAC, BLC/BCA-1, MIP-1alpha, MIP-1 beta, MDC, TECK, TARC, RANTES, HCC-1, HCC-4, DC-CK1, MIP-3 alpha, MIP-3 beta, MCP-1-5, eotaxin, Eotaxin-2, 1-309, MPIF-1, 6Ckine, CTACK, MEC, lymphotactin and fractalkine.

Examples of a pro-coagulant factor are tissue factor (TF) and cancer procoagulant (CP).

Examples of an enzyme for pro-drug activation are enzymes such as carboxy-peptidases, glucuronidases or glucosidases.

Examples of an albumin binder, and an IgG binder are described in Gebauer and Skerra (2009), Curr Opin Chem Biol., 13(3):245-255. Accordingly, examples of albumin binders and an IgG binders are human single Ig domains (dubbled Albumin Dab), nanobodies, naturally occurring albumin binding domain (ABD) derived from streptococcal protein G, and a domain that binds to IgG. Such fusion constructs, for example, increase the half life of the polypeptide of the invention upon administration to a patient, in particular in the blood circulation system.

In accordance with other embodiments of the second aspect of the invention, the further compound of the invention comprises an antibody light chain, an antibody heavy chain, an Fc domain of an antibody, an antibody, or a combination thereof.

The term "antibody" includes monoclonal antibodies, single chain antibodies, or fragments thereof, also including bispecific antibodies, synthetic antibodies, antibody fragments retaining the binding capacity other than heavy and light chains, such as Fab, a F(ab2)', Fv or scFv fragments etc., or a chemically modified derivative of any of these. Antibodies or fragments thereof can for instance be obtained by using methods which are described, e.g., in Harlow and Lane "Antibodies, A Laboratory Manual", CSH Press, Cold Spring Harbor, 1988. When derivatives of said antibodies are obtained by the phage display technique, surface plasmon resonance as employed in the BIAcore system can be used to increase the efficiency of phage antibodies which bind to an epitope of the peptide or polypeptide of the invention (Schier, Human Antibodies Hybridomas 7 (1996), 97-105; Malmborg, J. Immunol. Methods 183 (1995), 7-13). The production of chimeric antibodies is described, for example, in WO89/09622. A further source of antibodies to be utilized in accordance with the present invention are so-called xenogenic antibodies. The general principle for the production of xenogenic antibodies such as human antibodies in mice is described in, e.g., WO 91/10741, WO 94/02602, WO 96/34096 and WO 96/33735. Antibodies to be employed in accordance with the invention or their corresponding immunoglobulin chain(s) can be further modified using conventional techniques known in the art, for example, by using amino acid deletion(s), insertion(s), substitution(s), addition(s), and/or recombination(s) and/or any other modification(s) known in the art either alone or in combination. Methods for introducing such modifications in the DNA sequence underlying the amino acid sequence of an immunoglobulin chain are well known to the person skilled in the art; see, e.g., Sambrook, Molecular Cloning: A Laboratory Manual, Cold Spring Harbor Laboratory, Cold Spring Harbor, N.Y., 1989.

The term antibody also relates to derivatives of said antibodies which retain or essentially retain their binding specificity. Whereas particularly preferred embodiments of said derivatives are specified further herein below, other preferred derivatives of such antibodies are chimeric antibodies comprising, for example, a mouse or rat variable region and a human constant region.

The antibody may be a humanized antibody. The term "humanized antibody" means, in accordance with the present invention, an antibody of non-human origin, whose protein sequences has been modified to increase its similarity to antibody variants produced naturally in humans. Creation of a humanized antibody may be accomplished, for example, by inserting the appropriate CDR coding segments (responsible for the desired binding properties), such as CDR 3 and preferably all 6 CDRs, into a human antibody "scaffold". Methods for the production of humanized antibodies are described in, e.g., EP-A1 0 239 400 and WO 90/07861.

The term "antibody light chain" designates the small polypeptide subunit of an antibody while the term "antibody heavy chain" designates the large polypeptide subunit of an antibody. A typical antibody is composed of two immunoglobulin (Ig) heavy chains and two Ig light chains. Each light chain is composed of two tandem immunoglobulin domains; one constant ($C_L$) domain and one variable domain ($V_L$) that is important for binding antigen. The heavy chain determines the class or isotype of an antibody. Each heavy chain has two regions, namely a constant region (which is the same for all immunoglobulins of the same class but differs between classes) and a variable region that differs between different B cells, but is the same for all immunoglobulins produced by the same B cell or B cell clone. The variable domain of any heavy chain is composed of a single immunoglobulin domain.

A "functional Fc domain" of an antibody is a term well known to the skilled artisan and defined on the basis of papain cleavage of antibodies. Depending on the amino acid sequence of the constant region of their heavy chains, immunoglobulins are divided in the classes: IgA, IgD, IgE, IgG and IgM, and several of these may be further divided into subclasses (isotypes), e.g. IgG1, IgG2, IgG3, and IgG4, IgA1, and IgA2. According to the heavy chain constant regions the different classes of immunoglobulins are called [alpha], [delta], [epsilon], [gamma], and [mu], respectively. The functional Fc domain of an antibody is directly involved in ADCC (antibody-dependent cell-mediated cytotoxicity) and CDC (complement-dependent cytotoxicity) based on complement activation, C1q binding and Fc receptor binding. The four human IgG isotypes bind different receptors, such as the neonatal Fc receptor, the activating Fc gamma receptors, FcγRI, FcγRIIa, and FcγRIIIa, the inhibitory receptor FcγRIIb, and C1q with different affinities, yielding very different activities. It is known that the affinities to activating and inhibiting receptors of an Fc domain of a human antibody can be engineered and modified (see Strohl W. (2009) Curr Opin Biotechnol, 20, p. 685-691).

Preferably, the Fc domain is one or more human functional Fc domains which allow(s) for extending the in vivo half-life of the polypeptides of the invention and some of which direct a mammal's immune response to a site of specific target binding of the inventive polypeptide component of the fusion protein, e.g. in therapeutic, prophylactic and/or diagnostic applications as described herein below. More preferably such a human functional Fc domain is of an IgG1 antibody. The polypeptides of the invention can be fused either to the N- or C-terminus of one or more functional Fc domains or to both the N- and the C-terminus of one or more Fc domains. In certain embodiments, the fusion proteins of the invention may also comprise multimers, e.g. tetramers, trimers or dimers of the polypeptides of the invention fused to at least one side, e.g. to the N-terminus of an Fc domain.

The Fc domain may be one or more engineered human functional Fc domains of an IgG1 with activating or silenced effector functions, e.g. one or more engineered human functional Fc domains of an IgG1 with silenced effector functions, e.g. one or more engineered human functional Fc domains of an IgG1 with silenced effector functions with a mutation in L234 and L235, numbering according to EU index of Kabat (see Johnson G. and Wu T. T. (2000) Nucleic Acids Res. 28, p. 214-218), e.g. with the mutation L234A and L235A.

The polypeptide of the invention may be located downstream of the C-terminus of said further compound comprising an antibody light chain, an antibody heavy chain, an Fc domain of an antibody, an antibody, or a combination thereof. Alternatively, the polypeptide of the invention may be located downstream of the N-terminus of said further compound comprising an antibody light chain, an antibody heavy chain, an Fc domain of an antibody, an antibody, or a combination thereof.

In case the fusion construct of the invention comprises the polypeptide of the invention fused to an antibody, the fusion construct of the invention preferably comprises two copies of the polypeptide of the invention. The two copies may either be two copies of the same polypeptide of the invention or of different polypeptides of the invention and are preferably two copies of the same polypeptide of the invention.

More preferably, the two copies of the polypeptide of the invention may be fused to the N-terminus of the two light chains of the antibody, the C-terminus of the two light chains of the antibody, the N-terminus of the two heavy chains of the antibody, or the C-terminus of the two heavy chains of the antibody. Examples of Fynomers that are fused to monoclonal antibodies, creating so-called Fynomabs, which have dual specificity, and the preparation thereof, have been amply described for instance in (e.g. Silacci et al, 2016, mAbs 8:1, 141-149; Brack et al, 2014, Mol Cancer Ther 13(8): p. 2030-9; WO 2014/044758 A1; WO 2014/170063 A1; WO 2015/141862 A1).

A fusion construct according to the present invention that comprises the polypeptide of the invention fused to an antibody may be obtained ex vivo or in vitro by bringing together, under suitable conditions, the light and the antibody heavy chains of an antibody noting that the polypeptide of the invention is fused to at least one of these chains. The skilled person is aware of suitable conditions. Such bringing together under suitable conditions provides for the non-covalent assembly triggered by the interactions between the antibody light chains and the antibody heavy chains. Preferably, disulfide bonds as they are commonly found in antibodies are present in such a construct of the invention. Disulfide bonds are typically present in the proximity of the hinge region and connect two heavy chains and/or a light chain and a heavy chain. For instance, such constructs can be prepared by standard recombinant expression in mammalian cells, and typically intact fusion proteins of the invention comprising intact, paired, antibodies are then secreted from the cells.

In accordance with certain non-limiting embodiments of the second aspect of the invention, the antibody is directed against a target selected from the group consisting of GM-2, CD38, ICAM-1, SLAMF7, CD45, CD40, CD74, IGFR-1, CD20, BAFF, BCMA, CD66, GRP78, CXCR4, EGFR, EPCAM, TROP-2, B7H3 and CEACAM-1.

The further compound of the invention may thus also comprise an antibody light chain, an antibody heavy chain, or an antibody being directed against a target selected from the group consisting of GM-2, CD38, ICAM-1, SLAMF7, CD45, CD40, CD74, IGFR-1, CD20, BAFF, BCMA, CD66, GRP78, CXCR4, EGFR, EPCAM, TROP-2, B7H3 or CEACAM-1.

As discussed herein above, FGFR3 overexpression has been documented in several cancer types. Also the overexpression of GM-2, CD38, ICAM-1, SLAMF7, CD45, CD40, CD74, IGFR-1, CD20, BAFF, BCMA, CD66, GRP78, CXCR4, EGFR, EPCAM, TROP-2, B7H3 and CEACAM-1 has been documented in several cancer types. For this reason, bispecific fusion constructs being capable of binding FGFR3b/3c as first target as well as a second target which is a compound selected from GM-2, CD38, ICAM-1, SLAMF7, CD45, CD40, CD74, IGFR-1, CD20, BAFF, BCMA, CD66, GRP78, CXCR4, EGFR, EPCAM, TROP-2, B7H3 and CEACAM-1 are expected to be particularly suitable for treating cancer and related diseases.

The further compound described herein above may either be directly fused to the polypeptide of the invention or via a linker. Accordingly, the polypeptide may be (directly) fused, for example, to the C-terminus of the further compound, more specifically by the formation of a peptide bond between the carboxy group of the C-terminal amino acid and the amino group of the N-terminal amino acid, or may be connected to the C-terminus of the further compound chain via a linker.

Suitable linkers are at the skilled person's disposal. The linker according to the invention can for instance be selected from the group consisting of alkyl with 1 to 30 carbon atoms, polyethylene glycol with 1 to 20 ethylene moieties, polyalanine with 1 to 20 residues, caproic acid, substituted or unsubstituted poly-p-phenylene and triazol. Preference is given to peptidic linkers, more specifically to oligopeptides having a length from 1 to 30 amino acids. Preferred length ranges are from 5 to 15 amino acids.

Particularly preferred are linkers which are peptides which consist of at least 50%, at least 60%, at least 70%, at least 80%, at least 90% or 100% of small amino acids such as glycine, serine and alanine. Particularly preferred are linkers consisting of glycines and serines only. A non-limiting example of a suitable linker is a $(G4S)_3$ linker (3 repeats of Gly-Gly-Gly-Gly-Ser).

In a third aspect the present invention relates to a nucleic acid molecule encoding the polypeptide of the invention, or the fusion construct of the invention, or one or more nucleic acid molecules encoding the fusion construct of the invention.

The one or more nucleic acid molecules encoding the construct of the invention may be, for example, two nucleic acid molecules wherein one nucleic acid molecule encodes the light chain of an antibody and the other nucleic acid molecule the heavy chain of an antibody. As discussed above, the polypeptide of the invention may in this case be fused either to the light or the heavy chain, C-terminally or N-terminally.

Nucleic acid molecules, in accordance with the present invention, include DNA, such as cDNA, and mRNA as well as PNA. Further included are nucleic acid mimicking molecules known in the art such as synthetic or semisynthetic derivatives of DNA or RNA and mixed polymers, both sense and antisense strands. They may contain additional non-natural or derivatized nucleotide bases, as will be readily appreciated by those skilled in the art. In a preferred embodiment the polynucleotide or the nucleic acid molecule (s) is/are DNA. Such nucleic acid mimicking molecules or nucleic acid derivatives according to the invention include phosphorothioate nucleic acid, phosphoramidate nucleic acid, 2'-O-methoxyethyl ribonucleic acid, morpholino nucleic acid, hexitol nucleic acid (HNA) and locked nucleic acid (LNA) (see, for example, Braasch and Corey, Chemistry & Biology 8, 1-7 (2001)). LNA is an RNA derivative in which the ribose ring is constrained by a methylene linkage between the 2'-oxygen and the 4'-carbon.

In those embodiments where the nucleic acid molecule comprises (rather than consists of) the recited sequence, additional nucleotides extend over the specific sequence either on the 5' end or the 3' end or both.

Additional heterologous sequences may include heterologous promoters which are operatively linked to the coding sequences of above molecules. Hence, the nucleic acid molecule may be operably linked to a promoter. Promoters are well known to the skilled person and routinely used in the art. A non-limiting example is the CMV immediate early promoter, which typically drives strong expression in mammalian cells.

The present invention also relates to one or more vectors comprising one or more nucleic acid molecule of the invention as well as one or more host cells comprising the one or more nucleic acid molecule of the invention or the one or more vectors of the invention.

In addition, the invention relates to a cell, preferably an isolated cell, comprising the nucleic acid molecule or vector of the invention. This cell is also referred to as host cell.

The vectors and isolated cells, in particular host cells, may be any conventional type that suits the purpose, e.g. production of polypeptides, and/or fusion constructs of the invention, and/or therapeutically useful vectors and host cells. The skilled person will be able to select those vectors and host cells from the art and confirm their particular suitability for the desired purpose by routine methods and without undue burden.

The one or more vectors of the invention comprise one or more nucleic acids of the invention and are preferably capable of producing a polypeptide or fusion protein of the invention. In certain embodiments, such vectors are selected from the group consisting of pQE vectors, pET vectors, pFUSE vectors, pUC vectors, YAC vectors, phagemid vectors, phage vectors, vectors used for gene therapy such as retroviruses, adenoviruses, adeno-associated viruses. For vector modification techniques, see Sambrook and Russel, Molecular Cloning: A Laboratory Manual, 3rd ed., Cold Spring Harbor Laboratory Press, 2001. Generally, vectors can contain one or more origin of replication (ori) and inheritance systems for cloning or expression, one or more markers for selection in the host, e.g., antibiotic resistance, and one or more expression cassettes. Suitable origins of replication (ori) include, for example, the Col E1, the SV40 viral and the M13 origins of replication.

The one or more nucleic acid molecules of the present invention may also be inserted into one or more vectors such that a translational fusion with another nucleic acid molecule is generated. The other nucleic acid molecule can for instance encode the light and/or heavy chain of an antibody and/or a linker, preferred examples of which are described herein above.

The one or more host cells may be produced by introducing the one or more nucleic acid molecules or one or more vectors of the invention into the one or more host cells which upon their presence mediates the expression of the polypeptides encoded by said nucleic acid molecules or vectors. The host cells are preferably isolated host cells, meaning that the cells are not within the context of a living organism. The host may be any prokaryotic or eukaryotic cell. A suitable eukaryotic host may be a mammalian cell, an amphibian cell, a fish cell, an insect cell, a fungal cell or a plant cell. A eukaryotic cell may be an insect cell such as a *Spodoptera frugiperda* cell, a yeast cell such as a *Saccharomyces cerevisiae* or *Pichia pastoris* cell, a fungal cell such as an *Aspergillus* cell or a vertebrate cell. In the latter regard, it is preferred that the cell is a mammalian cell such as for instance a human cell, a hamster cell or a monkey cell. The cell may be a part of a cell line.

Suitable examples of prokaryotes/bacteria are those generally used for cloning like *E. coli* (e.g., *E coli* strains HB101, DH5a, XL1 Blue, Y1090 and JM101).

In a fourth aspect the present invention relates to a pharmaceutical or diagnostic composition comprising the polypeptide of the invention, the fusion construct of the invention, the nucleic acid molecule of the invention, or any combination thereof.

Pharmaceutical compositions of the invention preferably comprise a pharmaceutically acceptable carrier or excipient. By "pharmaceutically acceptable carrier or excipient" is meant a non-toxic solid, semisolid or liquid filler, diluent, encapsulating material or formulation auxiliary of any type. Examples of pharmaceutically acceptable carriers or excipients are described, e.g., in Ansel et al., "Pharmaceutical Dosage Forms and Drug Delivery Systems", 7th edition, Lippincott Williams & Wilkins Publishers, 1999.

As discussed in more detail herein above, FGFR3 is involved in many diseases and in particular cancer. Accordingly, the polypeptide, fusion construct, nucleic acid molecule, vector, of the invention or any combination thereof is useful as a medicament. Within said pharmaceutical composition the polypeptide, fusion construct, nucleic acid molecules, vector of the invention or any combination thereof may be the only active agent, but alternatively they could also be combined with other active agents, such as in combination products. The pharmaceutical composition can for instance be administered to mammals such as domestic and pet animals, mice, rats, rabbits, non-human primates, and the like. Preferably it is administered to humans. The pharmaceutical compositions described herein will be administered to the subject at a suitable dose.

The pharmaceutical composition for use in accordance with the present invention can be formulated in conventional manner according to methods found in the art, using one or more physiological carriers or excipient, see, for example Ansel et al., "Pharmaceutical Dosage Forms and Drug Delivery Systems", 7th edition, Lippincott Williams & Wilkins Publishers, 1999. The pharmaceutical composition may, accordingly, be administered orally, parenterally, such as subcutaneously, intravenously, intramuscularly, intraperitoneally, intrathecally, transdermally, transmucosally, subdurally, locally or topically via iontopheresis, sublingually, by inhalation spray, aerosol or rectally and the like in dosage unit formulations optionally comprising conventional pharmaceutically acceptable excipients. Also diagnostic compositions of the invention may be manufactured in any conventional manner.

The pharmaceutical composition of the invention may be administered as the sole active ingredient or in conjunction with another active ingredient, such as immunosuppressive or immune modulating agents or other anti-inflammatory agents, e.g. for the treatment or prevention of diseases mentioned above. For example, the polypeptides, fusion constructs and constructs of the invention may be used in combination with monoclonal antibodies, e.g. monoclonal antibodies with affinity to GM-2, CD38, ICAM-1, SLAMF7, CD45, CD40, CD74, IGFR-1, CD20, BAFF, BCMA, CD66, GRP78, CXCR4, EGFR, EPCAM, TROP-2, B7H3 or CEACAM-1.

The diagnostic composition of the invention is useful in the detection of an undesired physiological FGFR3 level, in particular due to an unwanted overexpression of FGFR3. Said detection typically comprises contacting a sample with the polypeptide, fusion construct, construct, nucleic acid molecule, vector, host cell of the invention or any combination thereof, and detecting the presence of a FGFR3b and 3c, in particular FGFR3b and 3c of SEQ ID NOs 9 and 10 in the sample. Accordingly, the diagnostic composition of the invention may be used for assessing the onset or the disease status and in particular cancer or a related disease being associated with FGRF3 overexpression.

In one embodiment of the present invention described herein above, the polypeptide of the invention is linked to a fluorescent dye, a photosentisizer, a radionuclide, or a contrast agent for medical imaging. Such fusion constructs are particularly suitable for diagnostic applications. This is because FGFR3 is, for example, overexpressed in cancer, so that a detectably labeled polypeptide of the invention can be used to image a diseased body site, thereby diagnosing a subject as having cancer.

The dosage of the diagnostic and pharmaceutical compositions of the invention, will vary depending upon the particular polypeptide, fusion construct, construct, one or more nucleic acid molecules, one or more vectors of the invention or any combination thereof, the individual patient group or patient, the optional presence of further diagnostically or medically active compounds and the nature and severity of the disease to be diagnosed or treated. Typically, the diagnostic or pharmaceutical composition is used in dosages of about 0.01 mg to about 20 mg per kilogram body weight, e.g. about 0.1 mg to about 5 mg per kilogram body weight. Diagnostic or pharmaceutical compositions may be administered more than once, e.g.

to monitor the course of a disease in case of diagnostic composition or to prolong treatment in case of a pharmaceutical composition. For example, the frequency of administration of the diagnostic or pharmaceutical composition may be in the range of daily up to about once every 3 months, e.g. about once every 2 weeks up to about once every 10 weeks, e.g. once every 4 to 8 weeks. In certain embodiments, a dosage regimen involves the administration of the diagnostic or pharmaceutical compositions of the invention once per month to once every 2 to 3 months, or less frequently.

In accordance with certain embodiments, the pharmaceutical or diagnostic composition of the fourth aspect of the invention is for use in the treatment of cancer or a T-cell mediated disease.

As discussed herein above, overexpression of FGFR3 has been reported in a number of cancer types, so that the pharmaceutical or diagnostic compositions are particularly suitable for treating and diagnosing cancer. The cancer is therefore preferably a cancer, wherein the cancer cell express FGFR3 on their surface or a cancer being associated with FGRF3 overexpression.

Due to the known role of FGFR3 expression in cancer the pharmaceutical or diagnostic composition of the invention may also be used in the treatment of neoplasias in general, including benign and malignant tumours.

It has been reported in US 2008/044419 that the inhibition of FGFR3 activity is a means of treating T-cell mediated diseases, in particular T-cell mediated inflammatory and autoimmune diseases.

In accordance with certain embodiments of the fourth aspect of the invention, the cancer is selected from breast cancer, cervical cancer, colorectal cancer, endometrial cancer, glioma, head and neck cancer, liver cancer, lung cancer, ovarian cancer, pancreatic cancer, skin cancer, testis cancer and urothelial cancer.

According to "The human protein Atlas" (see www.proteinatlas.org/ENSG00000068078-FGFR3/cancer) FGFR3 expression was found in the following cancer types: breast cancer, cervical cancer, colorectal cancer, endometrial cancer, glioma, head and neck cancer, liver cancer, lung cancer, ovarian cancer, pancreatic cancer, skin cancer, testis cancer and urothelial cancer. It therefore can be expected that that the expression of FGFR3 has an implication in the development of these cancer types.

In accordance with certain embodiments of the fourth aspect of the invention, the cancer is selected from multiple myeloma, bladder cancer, cervix cancer, pancreatic cancer, squamous cell lung cancer, and colorectal cancer.

It has been discussed herein above that the overexpression of FGFR3 has been reported in multiple myeloma as well as bladder cancer. The expression of FGFR3 is also implicated in cervix cancer, (Capellen et al., Nat Genet. 1999 September; 23(1):18-20), pancreatic cancer (Lafitte et al., Mol Cancer, 2013, 12:83), and colorectal cancer (Sonvilla et al., Br J Cancer, 2010; 102(7):1145-1156). Moreover, expression of FGFR3 was observed in squamous cell lung cancer (Liao et al (2013), Cancer Research, 73(16):5195-5205).

In accordance with certain embodiments of the fourth aspect of the invention, the T-cell mediated disease is selected from rheumatoid arthritis (RA), collagen II arthritis, multiple sclerosis (MS), systemic lupus erythematosus (SLE), psoriasis, juvenile onset diabetes, Sjögren's disease, thyroid disease, sarcoidosis, autoimmune uveitis, inflammatory bowel disease (Crohn's and ulcerative colitis), celiac disease and myasthenia gravis.

The above-listed diseases are non-limiting examples of particular T-cell mediated diseases that can be treated by the inhibition of FGFR3.

In this specification, a number of documents including patent applications and manufacturer's manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

Throughout this invention the term "comprising" means that all elements listed are encompassed. When this term is used, additional, unnamed elements may optionally also be present. Thus, "comprising" may mean "consisting of" (i.e. only the elements listed are present) or it may mean "containing" (i.e. also other elements besides all the elements listed are present). Thus, a polypeptide comprising SEQ ID NO: x may either consist of SEQ ID NO: x only, or may in other embodiments comprise additional amino acids, such as for instance in a fusion protein, for instance in embodiments where SEQ ID NO: x is fused to an antibody heavy or light chain.

Unless otherwise defined, all technical and scientific terms used herein have the same meaning as commonly understood by one of ordinary skill in the art to which this invention belongs. In case of conflict, the patent specification, including definitions, will prevail.

Regarding the embodiments characterized in this specification, in particular in the claims, it is intended that each embodiment mentioned in a dependent claim is combined with each embodiment of each claim (independent or dependent) said dependent claim depends from. For example, in case of an independent claim 1 reciting 3 alternatives A, B and C, a dependent claim 2 reciting 3 alternatives D, E and F and a claim 3 depending from claims 1 and 2 and reciting 3 alternatives G, H and I, it is to be understood that the specification unambiguously discloses embodiments corresponding to combinations A, D, G; A, D, H; A, D, I; A, E, G; A, E, H; A, E, I; A, F, G; A, F, H; A, F, I; B, D, G; B, D, H; B, D, I; B, E, G; B, E, H; B, E, I; B, F, G; B, F, H; B, F, I; C, D, G; C, D, H; C, D, I; C, E, G; C, E, H; C, E, I; C, F, G; C, F, H; C, F, I, unless specifically mentioned otherwise.

Similarly, and also in those cases where independent and/or dependent claims do not recite alternatives, it is understood that if dependent claims refer back to a majority of preceding claims, any combination of subject-matter covered thereby is considered to be explicitly disclosed. For example, in case of an independent claim 1, a dependent claim 2 referring back to claim 1, and a dependent claim 3 referring back to both claims 2 and 1, it follows that the combination of the subject-matter of claims 3 and 1 is clearly and unambiguously disclosed as is the combination of the subject-matter of claims 3, 2 and 1. In case a further dependent claim 4 is present which refers to any one of claims 1 to 3, it follows that the combination of the subject-matter of claims 4 and 1, of claims 4, 2 and 1, of claims 4, 3 and 1, as well as of claims 4, 3, 2 and 1 is clearly and unambiguously disclosed.

The above considerations apply mutatis mutandis to all appended claims. The figures show:

FIG. 1: Alignment of the anti-FGFR3 Fynomers of SEQ ID NOs 3 to 8.

FIG. 2: Internalization properties of anti-FGFR3 Fynomers.

FIG. 3: Size exclusion profiles of Fyn SH3-derived FGFR3-binding polypeptides: A) FF2L4C3—SEQ ID NO. 3; B) FF44L65G12—SEQ ID NO. 4; C) FF44L65G7—SEQ ID NO. 5; D) FF48L66G7—SEQ ID NO. 6; E) FF43L65D5—SEQ ID NO. 7; F) FF44L65B7—SEQ ID NO. 8.

FIG. 4: FACS binding of Fyn-SH3 derived polypeptides binding to FGFR3 to: A) FGFR3-positive KMS-11 cells and B) FGFR3-negative N87 cells.

FIG. 5: Specificity ELISA of Fyn SH3-derived FGFR3-binding polypeptides: A) FF2L4C3—SEQ ID NO. 3; B) FF44L65G12—SEQ ID NO. 4; C) FF44L65G7—SEQ ID NO. 5; D) FF48L66G7—SEQ ID NO. 6; E) FF43L65D5—SEQ ID NO. 7; F) FF44L65B7—SEQ ID NO. 8. Antigens tested: huFGFR3b=human FGFR3 splice variant b; huFGFR3c=human FGFR3 splice variant c; cyFGFR3c=cynomolgus FGFR3 splice variant c; muFGFR3c=murine FGFR3 splice variant c; huFGFR3-D1=domain 1 of human FGFR3; huFGFR3-D2=domain 2 of human FGFR3; huFGFR3-D1D2=domain 1 and domain 2 of human FGFR3; IgG=polyclonal human IgG mix; PBS=phosphate buffered saline solution.

FIG. 6: Internalization assay showing cytotoxic effect of Fyn SH3-derived FGFR3-binding polypeptides.

The examples illustrate the invention.

Example 1: Fyn SH3-Derived Polypeptides Binding to FGFR3b and FGFR3c

With the aim to be able to target FGFR3, we set out to obtain specific Fyn SH3-derived binding molecules thereto. Since the distribution and the expression of the two different splice variants (FGFR3b and FGFR3c) on different tumor cells is not fully understood, it is important that the Fyn SH3-derived polypeptides are able to bind both.

Using recombinant human FGFR3b-Fc (SEQ ID NO: 12) and FGFR3c-Fc (SEQ ID NO: 13) as targets, we successfully selected and isolated several families of Fyn SH3-derived binding proteins that are capable of binding to both splice variants of human FGFR3 (SEQ ID NOs 9 and 10). We continued with the most promising candidate family for further studies.

Interestingly, a Fyn SH3-derived polypeptide referred to as FF2L4C3 (SEQ ID NO: 3), carrying the RT-loop sequence "EVYGPTP" (SEQ ID NO: 2), was enriched during the selection process and showed the most promising internalization properties among 29 tested anti-FGFR3 Fynomers (see FIG. 2). In more detail, 5 other sequence families were excluded from further analysis. The Fynomers belonging to the most promising sequence family showed the best affinities and internalization properties.

In order to obtain Fyn SH3-derived FGFR3 binders with higher affinities and improved internalization properties, FF2L4C3 (SEQ ID NO: 3) was used as template for affinity maturation. The RT-loop sequence "EVYGPTP" (SEQ ID NO: 2) was kept constant and was combined with a randomized n-src-loop repertoire (where a stretch of 4 to 6 randomized amino acid residues were introduced at the positions (V) to ($X^4$) in SEQ ID NO: 1). The process of affinity maturation library generation was essentially the same as described for cloning of the naïve library with a randomized n-src-loop ("library 0" as described in [25]).

After naïve and affinity maturation selections, enriched Fyn SH3-derived polypeptides were screened for binding to FGFR3 by lysate ELISA. DNAs encoding the Fyn SH3-derived binding proteins were cloned into the bacterial expression vector pQE12 (Qiagen) so that the resulting constructs carried a C-terminal myc-hexahistidine tag as described in Grabulovski et al. [26]. The polypeptides were expressed in the cytosol of E. coli bacteria in a 96-well format and 200 µl of cleared lysate per well was prepared as described in Bertschinger et al. [27]. Briefly, transformed bacterial colonies were picked from the agar plate and grown in a round bottom 96-well plate (Nunc, cat. no. 163320) in 200 µl 2×YT medium containing 100 µg/ml ampicillin and 0.1% (w/v) glucose. Protein expression was induced after growth for 3 h at 37° C. and rotational shaking at 200 r.p.m. by adding 1 mM IPTG (Applichem, Germany). Proteins were expressed overnight in a rotary shaker (200 r.p.m., 30° C.). Subsequently, the 96-well plate was centrifuged at 1800 g for 10 min and the supernatant was discarded. Bacterial pellets were lysed using BugBuster® plus Benzonase® (Millipore 70750-3) and lysates were subsequently cleared by centrifugation for 10 min at 1800× g. 60 µl lysate were mixed with 170 µl PBS and filtered through a 0.45 µm Multiscreen filter plate (Millipore MSHVN4510), in order to eliminate any residual bacterial debris.

Monoclonal bacterial lysates were used for ELISA. For the ELISA, Maxisorp plates were coated overnight with either 5 µg/ml huFGFR3b-Fc (SEQ ID NO: 12), 5 µg/ml huFGFR3c-Fc (SEQ ID NO: 13) or 5 µg/ml poly IgG and blocked for at least 1 h with 2% MPBS. Cleared lysates containing soluble Fynomer with a C-terminal myc- and hexahistidine peptide tag were added in 2% MPBS containing murine monoclonal anti-myc tag antibody, clone 9E10 (Roche Applied Science 11 667 203 001) to the maxisorp plates. Bound Fynomer was detected via 9E10 by an anti-mouse IgG-horse radish peroxidase conjugate (Sigma-Aldrich A2554). The detection of peroxidase activity was done by adding BM blue POD substrate (Roche) and the reaction was stopped by adding 1 M $H_2SO_4$.

The DNA sequence of the specific binders was verified by DNA sequencing.

Results

The amino acid sequences of ELISA positive Fyn SH3-derived preferred polypeptides binding to FGFR3b and FGFR3c are presented in SEQ ID NOs: 3 to 8 as appended in the sequence listing. The Fyn-SH3 derived polypeptides SEQ ID NOs: 4 to 8 are a selection of binders from a large pool of molecules that were obtained after affinity maturation of FF2L4C3 (SEQ ID NO: 3), and are presented here because of their improved affinities and internalization properties (as shown in example 2 and 5).

In more detail, more than 80 Fynomers derived from SEQ ID NO: 3 were characterized with respect to their biophysical properties, affinities and internalization properties. SEQ ID NOs: 4 to 8 are the binders with the best set of properties in terms of biophysical, affinities and internalization.

Example 2: Expression of Fyn SH3-Derived FGFR3 Binding Polypeptides of the Invention This example shows the expression yields of the preferred Fyn SH3-derived FGFR3-binding polypeptides and the characterization of these polypeptides by size exclusion chromatography.

Methods a) Expression Yields of Fyn SH3-Derived FGFR3-Binding Polypeptides

Fyn SH3-derived FGFR3-binding polypeptides were expressed in the cytosol of TG1 E. coli bacteria and were purified as described in Grabulovski et al. [2].

b) Size Exclusion Chromatography (SEC)

Samples were analyzed by size exclusion chromatography (TOSOH TSKgel PW G3000PWxL; Agilent 1260 Infinity HPLC; PBS pH 7.4 mobile phase). 10 µl of undiluted sample was injected onto the column, and the resulting profiles were analyzed.

Results a) Expression Yields

The expression yields for monomeric Fyn SH3-derived FGFR3-binding polypeptides of the invention ranged from 15 to 51 mg/liter of bacterial culture under non-optimized conditions in shake flasks (Table 1), and are in a typical range for a Fyn SH3-derived polypeptide.

TABLE 1

Expression yields of Fyn SH3-derived FGFR3-binding polypeptides produced in TG1 E. coli bacteria

| Fynomer | SEQ ID NO | Yield (mg/l) |
| --- | --- | --- |
| FF2L4C3 | 3 | 18 |
| FF44L65G12 | 4 | 37 |
| FF44L65G7 | 5 | 15 |
| FF48L66G7 | 6 | 58 |
| FF43L65D5 | 7 | 32 |
| FF44L65B7 | 8 | 51 | b) Size Exclusion Chromatography (SEC)

Size exclusion chromatography (SEC) profiles demonstrated that all constructs eluted mainly as single, monomeric peaks (FIG. 3). This generally indicates good biophysical properties, which is advantageous from manufacturing perspective of Fynomers (Fyn SH3-derived binding molecules, including Fynomabs, which are fusion proteins with antibodies), and is in line with earlier observations of Fyn SH3-derived molecules.

Example 3: Fyn SH3-Derived Polypeptides of the Invention Bind to Human FGFR3b and FGFR3c with High Affinities This example shows the characterization of the preferred Fyn SH3-derived FGFR3-binding polypeptides by surface plasmon resonance and flow cytometry experiments.

Methods a) Affinity Measurements by BIAcore

Affinities were measured using a BIAcore T200 instrument. One flow cell on a CM5 series S chip (GE Healthcare BR-1005-30) was coated with the anti—myc antibody 9E10 (Roche 11 667 203 001; coating density ranging between 6000 and 8000 RU) using the amine coupling kit (GE Healthcare BR100633).

The parental Fynomer FF2L4C3 (SEQ ID NO:3), at a concentration of 500 nM, and the Fynomers with SEQ ID NOs: 4-8, at a concentration of 100 nM, were captured on the 9E10 surface followed by injections of different concentrations of huFGFR3b-Fc (SEQ ID NO: 12), huFGFR3c-Fc (SEQ ID NO: 13) or cynoFGFR3c-Fc (SEQ ID NO: 14) (0 nM, 3.9 nM, 7.8 nM, 15.6 nM, 31.25 nM, 62.5 nM, 125 nM, 250 nM and 500 nM for the measurements of the parental Fynomer FF2L4C3, 0 nM, 0.046 nM, 0.14 nM, 0.41 nM, 1.2 nM, 3.7 nM, 11.1 nM, 33.3 nM and 100 nM for Fynomers with SEQ ID NO: 4-8). Sensograms were recorded and apparent kinetics constants were determined by curve fitting using the 1.1 Langmuir interaction model in the BIAevaluation 2.1 software.

b) Affinity Measurements by Flow Cytometry

Binding of Fynomers to huFGFR3 on cells was analyzed by flow cytometry using KMS-11 cells (JCRB1179) as FGFR3-positive cells and N87 (ATCC, CRL-5822) as a FGFR3-negative control cell line. Both KMS-11 and N87 cells were maintained in RPMI1640 medium (Invitrogen 52400-25). All media were supplemented with 25 U/ml penicillin, 25 µg/ml streptomycin and 10% FCS. To harvest the semi-adherent KMS-11 cells from a T150 flask, the supernatant was removed into a 50 ml falcon tube, and the cells were washed with 10 ml PBS, which was also added to the falcon tube. 2 ml of Accutase (Sigma A6964) was added to the flask, and incubated for 10 min at 37° C. The Accutase was inactivated with the addition of 10 ml medium and added to the falcon tube, which was then centrifuged (250× g, 5 min) to pellet the cells. The cells were resuspended in FACS buffer (PBS+1% FCS+0.2% sodium azide) to a cell concentration of $1 \times 10^6$ cells/ml and 100 µl was used per well ($1 \times 10^5$ cells/well) for the flow cytometry staining in a 96-well round bottomed plate (Nunc 163320). For adherent N87 cells the supernatant and wash were discarded, and only the Accutase-detached cells were collected and prepared.

Fynomers were co-incubated with the mouse anti-myc antibody (clone 9E10; Roche 11667149001) to allow cross linking of myc-tagged Fynomers prior to cell binding. Fynomers were diluted to 1 µM and co-incubated with 667 nM 9E10 anti-myc antibody (3:2 molar ratio) in FACS buffer, for approximately 10 minutes on ice.

This mixture was serially diluted 1 in 4 down to a Fynomer concentration of 0.06 nM (8 concentrations in total). Controls included the secondary antibody 9E10 only (no Fynomer; 667 nM 9E10), cells only (FACS buffer only) and an anti-FGFR3 antibody (R&D systems; cat. No. MAB766) at a concentration of 10 nM. Cells were centrifuged in the 96-well plate (250×g, 5 min) and were resuspended with the samples indicated above, before incubation on ice for 1 hr. The plate was centrifuged and washed (PBS+0.2% sodium azide), before centrifuging again. Then 50 µl of the secondary antibody anti-mIgG Alexa488 (Life Technologies A21202) was added to the cells at a concentration of 4 µg/ml, before incubating in the dark, on ice, for 45 min. The plate was centrifuged and washed twice with PBS+0.2% sodium azide, before resuspending in FACS buffer and FACS analysis (Millipore Guava easyCyte 8HT).

FACS data analysis was performed using Prism 6. The data was transformed (X=log X), and analysed using a non-linear fit, log(agonist) vs. response—Variable slope (4 parameters).

Results a) Affinity Measurements by BIAcore

The binding properties were analyzed by real-time interaction analysis on a BIAcore chip revealing the following dissociation constants (1(D) for selected FGFR3-binding polypeptides:

TABLE 2

Apparent kinetics constants of the binding of Fyn SH3-derived FGFR3-binding polypeptides to recombinant human FGFR3b, human FGFR3c and cynomolgus FGFR3c.

| Fynomer | SEQ ID NO. | huFGFR3b $KD_{app}$ (pM) | huFGFR3c $KD_{app}$ (pM) | cyFGFR3c $KD_{app}$ (pM) |
|---|---|---|---|---|
| FF2L4C3 | 3 | 4700 | 4600 | 5900 |
| FF44L65G12 | 4 | 690 | 685 | 110 |
| FF44L65G7 | 5 | 470 | 335 | 280 |
| FF48L66G7 | 6 | 260 | 190 | 210 |
| FF43L65D5 | 7 | 335 | 230 | 160 |
| FF44L65B7 | 8 | 100 | 250 | 260 |

The measured apparent affinities (Table 2) of the Fyn SH3-derived polypeptides (SEQ ID NOs: 3 to 8) binding to FGFR3b and FGFR3c (SEQ ID NOs 9 and 10) are surprisingly high considering the fact that sub-nanomolar values were obtained after only one round of affinity maturation. Moreover, these measurements confirmed the comparable binding properties of the Fyn SH3 derived polypeptides (SEQ ID NOs: 3 to 8) to both human isoforms of FGFR3 (FGFR3b and FGFR3c; SEQ ID NOs 9 and 10), and to cynomolgus FGFR3c (binding to cynomolgus FGFR3b was not tested).

b) Affinity Measurements by Flow Cytometry

The binding properties were analyzed by flow cytometry using FGFR3-positive KMS-11 cells and FGFR3-negative N87 cells as negative control. The following EC50 values for selected FGFR3-binding polypeptides were measured as shown in Table 3 and FIG. 4.

TABLE 3

EC50 values determined on FGFR3-positive KMS-11 cells for Fyn SH3-derived FGFR3-binding polypeptides.

| Fynomer | SEQ ID NO | EC50 (nM) |
|---|---|---|
| FF2L4C3 | 3 | 5.9 |
| FF44L65G12 | 4 | 2.2 |
| FF44L65G7 | 5 | 4.2 |
| FF48L66G7 | 6 | 2.3 |
| FF43L65D5 | 7 | 1.2 |
| FF44L65B7 | 8 | 0.6 |

EC50 values, in the low nanomolar range (Table 3), measured on a cell line expressing FGFR3 (FIG. 4A, KMS-11) confirmed the high apparent affinities measured by surface plasmon resonance (Table 2), and demonstrate binding to FGFR3 in the natural context of a cell surface. All the Fyn SH3-derived polypeptides (SEQ ID NOs: 3 to 8) binding to FGFR3 did not show unspecific binding on a cell line not expressing FGFR3 (FIG. 4B).

Example 4: Fyn SH3-Derived Polypeptides of the Invention Specific to FGFR3 do not Interfere with Ligand Binding It would be preferred if the Fyn SH3-derived polypeptides for binding both isoforms FGFR3b and FGFR3c to not interfere with ligand (e.g. FGF1) binding, as the ligand binding site is located in proximity to the splice site give rise to either FGFR3b or FGFR3c.

For the purpose of verifying the ability of the Fyn SH3-derived polypeptides to bind to FGFR3 in presence of one of its ligands, a BIAcore experiment was set up to measure the affinity of the Fynomers to FGFR3 in presence or absence of FGF1 (Fibroblast Growth Factor 1 is one of the major ligands of FGFR3).

In analogy to the method used for measuring the affinities (as described in Example 3) Fynomers at concentration of 100 nM (with the exception of FF2L4C3—SEQ ID NO. 3 used at a concentration of 500 nM) were captured on the 9E10 surface followed by injections of different concentrations of huFGFR3c-Fc (SEQ ID NO: 13) (0 nM, 11 nM, 33 nM, 100 nM) in presence or absence of 200 nM FGF1 (R&D systems 232-FA-025/CF). Sensograms were recorded and apparent kinetics constants were calculated using the BIAevaluation 2.1 software.

Results

Independently of the presence or absence of 200 nM FGF1 in solution binding of the Fyn SH3-derived polypeptides to huFGFR3c was unchanged, showing that binding of the Fynomers to FGFR3 did not interfere with ligand binding.

TABLE 4

Shows the kinetics constants obtained in presence or absence of 200 nM FGF1.

| Fynomer | SEQ ID NO. | KDapp (pM) to huFGFR3c-Fc (SEQ ID NO: 13) | $KD_{app}$ (pM) to huFGFR3c-Fc (SEQ ID NO: 13) in presence of 200 nM GF1 |
|---|---|---|---|
| FF2L4C3 | 3 | 4000 | 3800 |
| FF44L65G12 | 4 | 140 | 120 |
| FF44L65G7 | 5 | 320 | 230 |
| FF48L66G7 | 6 | 170 | 130 |
| FF43L65D5 | 7 | 60 | 70 |
| FF44L65B7 | 8 | 170 | 130 |

Even though, due to assay variability the values for $KD_{app}$ in absence of FGF1 are slightly different than the values obtained in the experiment shown in Example 2 (Table 2), this experiment shows that the Fyn SH3-derived polypeptides are able bind to FGFR3 even if the ligand (in this case FGF1) is bound to the ligand binding site.

From this we conclude that the epitope bound by the Fyn SH3-derived polypeptides described here is located in a constant region of FGFR3.

Example 5: Fyn SH3-Derived Polypeptides of the Invention Bind to the Domains D1-D2 of FGFR3

Specificity of Fyn-SH3 derived polypeptides binding to FGFR3 was tested by ELISA.

Different antigens were coated on the plate (Maxisorp plate; Nunc 439454): huFGFR3b-Fc (SEQ ID NO: 12), huFGFR3c-Fc (SEQ ID NO: 13), cyFGFR3c-Fc (SEQ ID NO: 14), muFGFR3c-His (SEQ ID NO: 15), huD1-Fc (SEQ ID NO: 16), huD2-Fc (SEQ ID NO: 17), huD1-D2-Fc (SEQ ID NO: 18).

The plate was coated with 100 ul antigen at 5 μg/ml (0.5 μg/well), and incubated at 4° C. overnight. The wells were washed 3× with PBS before being blocked with 200 μl 4% MPBS for 1 hr at RT. The wells were washed again, and 20 μl 10% MPBS containing 15 μg/ml 9E10 was added, before the addition of 80 μl Fynomer at 250 nM (200 nM final Fynomer concentration). The wells were incubated for 45 min at RT, before washing and the addition of 100 μl anti-mouse IgG-HRP (Sigma A2554) diluted 1:1000 in 2% MPBS. The wells were incubated for 30 min at RT, before washing 3× with 0.1% Tween-20 in PBS, and then 3×PBS. 100 μl BM POD Blue substrate (Roche 11 484 281 001) was added to each well followed by 50 μl 1M H2SO4 to stop the reaction. The absorbance 450 nm-650 nm was recorded using a Tecan M1000 instrument.

Results

As shown in FIG. 5 A-F, the Fyn SH3-derived polypeptides all are cross-reactive to cynomolgus and murine FGFR3c. Interestingly all binders are specific for an epitope present only when the domains D1 and D2 are physically linked (see FIG. 5 A-F bar huFGFR3-D1D2), in fact no binding is observed if the single domains D1 or D2 (hFGFR3-D1 or huFGFR3-D2) are immobilized on the ELISA plate.

Example 6: Fyn SH3-Derived Polypeptides of the Invention Cause Efficient Internalization of FGFR3

Internalization is a central feature of the Fyn SH3-derived polypeptides described here, and provides the opportunity to use these binders to deliver toxic payloads and/or fused proteins such as antibodies intracellularly.

In order to assess the ability of the Fyn SH3-derived polypeptides binding to FGFR3 to internalize upon binding to the target, an internalization assay based on the intracellular delivery of a cytotoxic agent was established.

The assay measures the cytotoxic effect of anti-FGFR3 Fynomers cross-linked with MMAF (Monomethyl auristatin F)-conjugated 9E10, on KMS-11 cells. MMAF is an antimitotic agent (blocks tubulin polymerization) and is active only upon internalization into the cells. Therefore, this assay indicates how well the Fynomer facilitates internalization of MMAF. 50 μl of KMS-11 cells at $2 \times 10^5$ cells/ml were seeded into a 96-well flat bottomed plate (Corning Costar 3610), to give 10,000 cell per well. The cells were incubated for 4 hours to allow the cells to adhere (37° C., 5% CO2). Fynomers and 9E10-MMAF were mixed at a 3:1 ratio. A 4× stock of Fynomer (4 μM) and a 4× stock of 9E10-MMAF (1.33 μM) were prepared in RPMI media (see section 5.4.1) and mixed 1:1 (40 μl+40 μl). This mixture was then serially diluted 1 in 3, to give a concentration range 1000 nM-50 pM. 50 μl of the sample was added to the 50 μl of cells (as seeded above), and incubated for 5 days (37° C., 5% CO2). Appropriate controls, the wild-type Fynomer FynSH3, MMAF-9E10 without Fynomer and also cells without addition of any reagents, were included. All samples were prepared in duplicate. After 5 days, 100 μl Cell titer glo (Promega G7573) was added to each well and incubated with gentle shaking for 10 min in the dark. As a read-out for cell viability, luminescence was measured using a Tecan M1000 instrument. Analysis was performed using Prism 6. The data was transformed (X=log X), and analysed using a non-linear fit, log(inhibitor) vs. response—Variable slope (4 parameters).

Results

All Fyn SH3-derived FGFR3-binding polypeptides described here show increased cytotoxicity (e.g. internalization) compared to the cells treated with the MMAF-labeled secondary antibody only (9E10 in FIG. 6A) or the wild-type Fynomer FynSH3 in combination with MMAF-labeled 9E10 shown in all 3 experiments (FIG. 6 A-C indicated as FynSH3), that show cytotoxicity only at the highest concentration tested, probably due to the toxicity of MMAF itself. FIG. 6 shows the cytotoxicity profiles obtained in different experiments, and Table 5 shows the EC50 obtained for the different Fyn SH3-derived FGFR3-binding polypeptides.

The data shown in FIG. 6 and Table 5 show that increased affinity also leads to more efficient internalization.

Example 7: Alternative Fyn-SH3 Derived Polypeptide that Shows Excellent Binding and Internalization Properties and which is Derived of a Different Family In addition to the preferred family of sequences (SEQ ID NO: 1), we identified one alternative Fynomer, FF40L54A5 (SEQ ID NO: 22), that surprisingly also shows excellent binding and internalization properties and shares manufacturability and cross-reactivity properties with the Fynomers derived from SEQ ID NO: 1 (see Table 6). Fynomer FF40L54A5 was not expected to have excellent internalization properties as its sequence derived from a Fynomer that showed only very poor internalization properties. Table 6 summarizes the properties of Fynomer FF40L54A5.

TABLE 6 part 1

| Fynomer | SEQ ID NO. | Yield (mg/L) | Affinities measured by BIAcore | | |
|---|---|---|---|---|---|
| | | | huFGFR3b $KD_{app}$ (pM) | huFGFR3c $KD_{app}$ (pM) | cyFGFR3c $KD_{app}$ (pM) |
| FF40L54A5 | 22 | 5.4 | 170 | 170* | 160 | part2

| Fynomer | SEQ ID NO. | EC50 (nM) for binding to FGFR3+ KMS-11 cells | Affinities measured by BIAcore (competition with FGF1) | | EC50 (nM) in internalization assay |
|---|---|---|---|---|---|
| | | | $KD_{app}$ (pM) to huFGFR3c-Fc | $KD_{app}$ (pM) to huFGFR3c-Fc in presence of 200 nM FGF1 | |
| FF40L54A5 | 22 | 6.6 | 210* | 230 | 4.7 | part 3

| Fynomer | SEQ ID NO. | Specificity ELISA | | | | |
|---|---|---|---|---|---|---|
| | | Cross-reactivity to cyFGFR3c | Cross-reactivity to muFGFR3c | Binding to domain D1 of huFGFR3 | Binding to domain D2 of huFGFR3 | Binding to domains D1-D2 of huFGFR3 |
| FF40L54A5 | 22 | +++ | +++ | − | − | +++ |

*differences due to experimental variability

TABLE 5

EC50 values determined in internalization assays using FGFR3 + KMS-11 cells for Fyn SH3-derived FGFR3-binding polypeptides.

| Fynomer | SEQ ID NO. | EC50 (nM) |
|---|---|---|
| FF2L4C3 | 3 | 28.5/21/26.4 |
| FF44L65G12 | 4 | 2.5 |
| FF44L65G7 | 5 | 2.6 |
| FF48L66G7 | 6 | 2.4 |
| FF43L65D5 | 7 | 0.8 |
| FF44L65B7 | 8 | 1.8 |

Note:
for FF2L4C3 the 3 values obtained in the 3 experiments shown in FIG. 6 are indicated.

REFERENCES

1. Turner, N. and R. Grose, *Fibroblast growth factor signalling: from development to cancer*. Nat Rev Cancer, 2010. 10(2): p. 116-29.
2. Kalff, A. and A. Spencer, *The t(4; 14) translocation and FGFR3 overexpression in multiple myeloma: prognostic implications and current clinical strategies*. Blood Cancer J, 2012. 2: p. e89.
3. Pollett, J. B., et al., *Overexpression of the myeloma-associated oncogene fibroblast growth factor receptor 3 confers dexamethasone resistance*. Blood, 2002. 100(10): p. 3819-21.
4. Fonseca, R., et al., *Clinical and biologic implications of recurrent genomic aberrations in myeloma*. Blood, 2003. 101(11): p. 4569-75.

5. Agazie, Y. M., et al., *The phosphotyrosine phosphatase SHP2 is a critical mediator of transformation induced by the oncogenic fibroblast growth factor receptor 3*. Oncogene, 2003. 22(44): p. 6909-18.
6. Ronchetti, D., et al., *Deregulated FGFR3 mutants in multiple myeloma cell lines with t(4; 14): comparative analysis of Y373C, K650E and the novel G384D mutations*. Oncogene, 2001. 20(27): p. 3553-62.
7. Chesi, M., et al., *Activated fibroblast growth factor receptor 3 is an oncogene that contributes to tumor progression in multiple myeloma*. Blood, 2001. 97(3): p. 729-36.
8. Plowright, E. E., et al., *Ectopic expression of fibroblast growth factor receptor 3 promotes myeloma cell proliferation and prevents apoptosis*. Blood, 2000. 95(3): p. 992-8.
9. Chen, J., et al., *Constitutively activated FGFR3 mutants signal through PLCgamma-dependent and-independent pathways for hematopoietic transformation*. Blood, 2005. 106(1): p. 328-37.
10. Li, Z., et al., *The myeloma-associated oncogene fibroblast growth factor receptor 3 is transforming in hematopoietic cells*. Blood, 2001. 97(8): p. 2413-9.
11. Trudel, S., et al., *Inhibition of fibroblast growth factor receptor 3 induces differentiation and apoptosis in t(4;14) myeloma*. Blood, 2004. 103(9): p. 3521-8.
12. Trudel, S., et al., *CHIR-258, a novel, multitargeted tyrosine kinase inhibitor for the potential treatment of t(4;14) multiple myeloma*. Blood, 2005. 105(7): p. 2941-8.
13. Chen, J., et al., *FGFR3 as a therapeutic target of the small molecule inhibitor PKC412 in hematopoietic malignancies*. Oncogene, 2005. 24(56): p. 8259-67.
14. Paterson, J. L., et al., *Preclinical studies of fibroblast growth factor receptor 3 as a therapeutic target in multiple myeloma*. Br J Haematol, 2004. 124(5): p. 595-603.
15. Grand, E. K., et al., *Targeting FGFR3 in multiple myeloma: inhibition of t(4;14)-positive cells by SU5402 and PD173074*. Leukemia, 2004. 18(5): p. 962-6.
16. Gomez-Roman, J. J., et al., *Fibroblast growth factor receptor 3 is overexpressed in urinary tract carcinomas and modulates the neoplastic cell growth*. Clin Cancer Res, 2005. 11(2 Pt 1): p. 459-65.
17. Tomlinson, D. C., et al., *FGFR3 protein expression and its relationship to mutation status and prognostic variables in bladder cancer*. J Pathol, 2007. 213(1): p. 91-8.
18. van Rhijn, B. W., et al., *Frequent FGFR3 mutations in urothelial papilloma*. J Pathol, 2002. 198(2): p. 245-51.
19. Tomlinson, D. C., C. D. Hurst, and M. A. Knowles, *Knockdown by shRNA identifies S249C mutant FGFR3 as a potential therapeutic target in bladder cancer*. Oncogene, 2007. 26(40): p. 5889-99.
20. Martinez-Torrecuadrada, J., et al., *Targeting the extracellular domain of fibroblast growth factor receptor 3 with human single-chain Fv antibodies inhibits bladder carcinoma cell line proliferation*. Clin Cancer Res, 2005. 11(17): p. 6280-90.
21. Martinez-Torrecuadrada, J. L., et al., *Antitumor activity of fibroblast growth factor receptor 3-specific immunotoxins in a xenograft mouse model of bladder carcinoma is mediated by apoptosis*. Mol Cancer Ther, 2008. 7(4): p. 862-73.
22. Rauchenberger, R., et al., *Human combinatorial Fab library yielding specific and functional antibodies against the human fibroblast growth factor receptor 3*. J Biol Chem, 2003. 278(40): p. 38194-205.
23. Brack, S., et al., *A bispecific HER2-targeting FynomAb with superior antitumor activity and novel mode of action*. Mol Cancer Ther, 2014. 13(8): p. 2030-9.
24. Silacci, M., et al., *Discovery and characterization of COVA322, a clinical-stage bispecific TNF/IL-17A inhibitor for the treatment of inflammatory diseases*. MAbs, 2016. 8(1): p. 141-9.
25. Schlatter, D., et al., *Generation, characterization and structural data of chymase binding proteins based on the human Fyn kinase SH3 domain*. MAbs, 2012. 4(4): p. 497-508.
26. Grabulovski, D., M. Kaspar, and D. Neri, *A novel, non-immunogenic Fyn SH3-derived binding protein with tumor vascular targeting properties*. J Biol Chem, 2007. 282(5): p. 3196-204.
27. Bertschinger, J., D. Grabulovski, and D. Neri, *Selection of single domain binding proteins by covalent DNA display*. Protein Eng Des Sel, 2007. 20(2): p. 57-68.

The invention claimed is:

1. A nucleic acid molecule encoding a polypeptide binding to fibroblast growth factor receptor 3 isoforms 3b and 3c (FGFR3b and FGFR3c), wherein the polypeptide comprises an amino acid sequence selected from the group consisting of:

(a)
(SEQ ID NO: 1)
GVTLFVALYDYEVYGPTPMLSFHKGEKFQIL($X^1$)($X^2$)($X^3$)($X^4$)GPYW
EARSL($X^5$)TGETG($X^6$)IPSNYVAPVDSIQ;

wherein amino acid positions ($X^1$) to ($X^6$) may be any amino acid sequence; and (b) an amino acid sequence which is at least 95% identical to the amino acid sequence of (a), wherein the identity determination excludes amino acid positions ($X^1$) to ($X^6$) and provided that the amino acid sequence EVYGPTPM (SEQ ID NO: 2) in amino acid positions 12 to 19 of SEQ ID NO: 1 is conserved and the amino acids P and Y in amino acid positions 37 and 38 of SEQ ID NO: 1 are conserved;

(c)
(SEQ ID NO: 19)
GVTLFVALYDYEVMSTTALSFHKGEKFQILSQSPHGQYWEARSLTTGETG
($X^6$)IPSNYVAPVDSIQ, wherein the amino acid position ($X^6$) may be any amino acid; and (d) an amino acid sequence which is at least 95% identical to the amino acid sequence of (c), wherein the identity determination excludes amino acid position ($X^6$) and provided that the amino acid sequences EVMSTTA (SEQ ID NO: 20) in amino acid positions 12 to 18 of SEQ ID NO: 19 and SQSPH (SEQ ID NO: 21) in amino acid positions 31 to 35 of SEQ ID NO: 19 are conserved and the amino acids Q and Y in amino acid positions 37 and 38 of SEQ ID NO: 19 are conserved.

2. The nucleic acid of claim 1, wherein
($X^1$) is N, R, or K, and is preferably R or K;
($X^2$) is S, G, K or R, and is preferably G, K or R;
($X^3$) is S or G, and is preferably G;
($X^4$) is E, Q, D, S or K, and is preferably Q, D, S or K;
($X^5$) is T or A; and
($X^6$) is Y, W or L, and is preferably L or W.

3. The nucleic acid of claim 1, wherein the polypeptide comprises an amino acid sequence selected from the group consisting of any one of SEQ ID NOs 3 to 8 and 22.

4. A nucleic acid encoding a fusion construct comprising the polypeptide of claim 3 fused to a further compound, wherein the further compound comprises an antibody light chain, an antibody heavy chain, an Fc domain of an antibody, an antibody, or a combination thereof.

5. The nucleic acid of claim 1, wherein the polypeptide comprises an amino acid sequence selected from the group consisting of:
SEQ ID NO: 4,
SEQ ID NO: 5,
SEQ ID NO: 6,
SEQ ID NO: 7,
SEQ ID NO: 8, and
SEQ ID NO: 22.

6. A nucleic acid encoding a fusion construct comprising the polypeptide of claim 5 fused to a further compound, wherein the further compound comprises an antibody light chain, an antibody heavy chain, an Fc domain of an antibody, an antibody, or a combination thereof.

7. A nucleic acid encoding a fusion construct comprising the polypeptide of claim 1 fused to a further compound, wherein the further compound comprises an antibody light chain, an antibody heavy chain, an Fc domain of an antibody, an antibody, or a combination thereof.

8. The nucleic acid of claim 7, wherein the antibody is directed against a target selected from the group consisting of GM-2, CD38, ICAM-1, SLAMF7, CD45, CD40, CD74, IGFR-1, CD20, BAFF, BCMA, CD66, GRP78, CXCR4, EGFR, EPCAM, TROP-2, B7H3 and CEACAM-1.

9. A vector comprising the nucleic acid molecule according to any one of claims 1 to 6.

10. An isolated cell comprising the vector of claim 9.

11. An isolated cell comprising the nucleic acid molecule according to any one of claims 1 to 6.

12. A method of producing the polypeptide encoded by the nucleic acid of any one of claims 1 to 6 comprising
(a) culturing the isolated cell comprising the nucleic acid; and
(b) isolating the produced polypeptide.

* * * * *

SEQUENCE LISTING

```
<160> NUMBER OF SEQ ID NOS: 22

<210> SEQ ID NO 1
<211> LENGTH: 64
<212> TYPE: PRT
<213> ORGANISM: Artificial Sequence
<220> FEATURE:
<223> OTHER INFORMATION: Consensus sequence anti-FGFR3 Fynomers
<220> FEATURE:
<221> NAME/KEY: VARIANT
<222> LOCATION: 32
<223> OTHER INFORMATION: any amino acid
<220> FEATURE:
<221> NAME/KEY: VARIANT
<222> LOCATION: 33
<223> OTHER INFORMATION: any amino acid
<220> FEATURE:
<221> NAME/KEY: VARIANT
<222> LOCATION: 34
<223> OTHER INFORMATION: any amino acid
<220> FEATURE:
<221> NAME/KEY: VARIANT
<222> LOCATION: 35
<223> OTHER INFORMATION: any amino acid
<220> FEATURE:
```

```
<221> NAME/KEY: VARIANT
<222> LOCATION: 45
<223> OTHER INFORMATION: any amino acid
<220> FEATURE:
<221> NAME/KEY: VARIANT
<222> LOCATION: 51
<223> OTHER INFORMATION: any amino acid

<400> SEQUENCE: 1

Gly Val Thr Leu Phe Val Ala Leu Tyr Asp Tyr Glu Val Tyr Gly Pro
1               5                   10                  15

Thr Pro Met Leu Ser Phe His Lys Gly Glu Lys Phe Gln Ile Leu Xaa
            20                  25                  30

Xaa Xaa Xaa Gly Pro Tyr Trp Glu Ala Arg Ser Leu Xaa Thr Gly Glu
        35                  40                  45

Thr Gly Xaa Ile Pro Ser Asn Tyr Val Ala Pro Val Asp Ser Ile Gln
    50                  55                  60

<210> SEQ ID NO 2
<211> LENGTH: 8
<212> TYPE: PRT
<213> ORGANISM: Artificial Sequence
<220> FEATURE:
<223> OTHER INFORMATION: RT-loop sequence

<400> SEQUENCE: 2

Glu Val Tyr Gly Pro Thr Pro Met
1               5

<210> SEQ ID NO 3
<211> LENGTH: 64
<212> TYPE: PRT
<213> ORGANISM: Artificial Sequence
<220> FEATURE:
<223> OTHER INFORMATION: FF2L4C3 anti-FGFR3 Fynomer

<400> SEQUENCE: 3

Gly Val Thr Leu Phe Val Ala Leu Tyr Asp Tyr Glu Val Tyr Gly Pro
1               5                   10                  15

Thr Pro Met Leu Ser Phe His Lys Gly Glu Lys Phe Gln Ile Leu Asn
            20                  25                  30

Ser Ser Glu Gly Pro Tyr Trp Glu Ala Arg Ser Leu Thr Thr Gly Glu
        35                  40                  45

Thr Gly Leu Ile Pro Ser Asn Tyr Val Ala Pro Val Asp Ser Ile Gln
    50                  55                  60

<210> SEQ ID NO 4
<211> LENGTH: 64
<212> TYPE: PRT
<213> ORGANISM: Artificial Sequence
<220> FEATURE:
<223> OTHER INFORMATION: FF44L65G12 anti-FGFR3 Fynomer

<400> SEQUENCE: 4

Gly Val Thr Leu Phe Val Ala Leu Tyr Asp Tyr Glu Val Tyr Gly Pro
1               5                   10                  15

Thr Pro Met Leu Ser Phe His Lys Gly Glu Lys Phe Gln Ile Leu Arg
            20                  25                  30

Gly Gly Gln Gly Pro Tyr Trp Glu Ala Arg Ser Leu Thr Thr Gly Glu
        35                  40                  45

Thr Gly Leu Ile Pro Ser Asn Tyr Val Ala Pro Val Asp Ser Ile Gln
    50                  55                  60
```

<210> SEQ ID NO 5
<211> LENGTH: 64
<212> TYPE: PRT
<213> ORGANISM: Artificial Sequence
<220> FEATURE:
<223> OTHER INFORMATION: FF44L65G7 anti-FGFR3 Fynomer

<400> SEQUENCE: 5

```
Gly Val Thr Leu Phe Val Ala Leu Tyr Asp Tyr Glu Val Tyr Gly Pro
1               5                   10                  15

Thr Pro Met Leu Ser Phe His Lys Gly Glu Lys Phe Gln Ile Leu Arg
            20                  25                  30

Gly Gly Asp Gly Pro Tyr Trp Glu Ala Arg Ser Leu Thr Thr Gly Glu
        35                  40                  45

Thr Gly Leu Ile Pro Ser Asn Tyr Val Ala Pro Val Asp Ser Ile Gln
    50                  55                  60
```

<210> SEQ ID NO 6
<211> LENGTH: 64
<212> TYPE: PRT
<213> ORGANISM: Artificial Sequence
<220> FEATURE:
<223> OTHER INFORMATION: FF48L66G7 anti-FGFR3 Fynomer

<400> SEQUENCE: 6

```
Gly Val Thr Leu Phe Val Ala Leu Tyr Asp Tyr Glu Val Tyr Gly Pro
1               5                   10                  15

Thr Pro Met Leu Ser Phe His Lys Gly Glu Lys Phe Gln Ile Leu Lys
            20                  25                  30

Gly Gly Ser Gly Pro Tyr Trp Glu Ala Arg Ser Leu Thr Thr Gly Glu
        35                  40                  45

Thr Gly Leu Ile Pro Ser Asn Tyr Val Ala Pro Val Asp Ser Ile Gln
    50                  55                  60
```

<210> SEQ ID NO 7
<211> LENGTH: 64
<212> TYPE: PRT
<213> ORGANISM: Artificial Sequence
<220> FEATURE:
<223> OTHER INFORMATION: FF43L65D5 anti-FGFR3 Fynomer

<400> SEQUENCE: 7

```
Gly Val Thr Leu Phe Val Ala Leu Tyr Asp Tyr Glu Val Tyr Gly Pro
1               5                   10                  15

Thr Pro Met Leu Ser Phe His Lys Gly Glu Lys Phe Gln Ile Leu Arg
            20                  25                  30

Lys Gly Lys Gly Pro Tyr Trp Glu Ala Arg Ser Leu Ala Thr Gly Glu
        35                  40                  45

Thr Gly Leu Ile Pro Ser Asn Tyr Val Ala Pro Val Asp Ser Ile Gln
    50                  55                  60
```

<210> SEQ ID NO 8
<211> LENGTH: 64
<212> TYPE: PRT
<213> ORGANISM: Artificial Sequence
<220> FEATURE:
<223> OTHER INFORMATION: FF44L65B7 anti-FGFR3 Fynomer

<400> SEQUENCE: 8

```
Gly Val Thr Leu Phe Val Ala Leu Tyr Asp Tyr Glu Val Tyr Gly Pro
1               5                   10                  15
```

```
Thr Pro Met Leu Ser Phe His Lys Gly Glu Lys Phe Gln Ile Leu Arg
            20                  25                  30

Arg Gly Ser Gly Pro Tyr Trp Glu Ala Arg Ser Leu Thr Thr Gly Glu
        35                  40                  45

Thr Gly Leu Ile Pro Ser Asn Tyr Val Ala Pro Val Asp Ser Ile Gln
    50                  55                  60
```

<210> SEQ ID NO 9
<211> LENGTH: 357
<212> TYPE: PRT
<213> ORGANISM: Homo sapiens
<220> FEATURE:
<223> OTHER INFORMATION: FGFR3, isoform b

<400> SEQUENCE: 9

```
Ile Ser Glu Ser Leu Gly Thr Glu Gln Arg Val Val Gly Arg Ala Ala
1               5                   10                  15

Glu Val Pro Gly Pro Glu Pro Gly Gln Gln Glu Gln Leu Val Phe Gly
            20                  25                  30

Ser Gly Asp Ala Val Glu Leu Ser Cys Pro Pro Pro Gly Gly Gly Pro
        35                  40                  45

Met Gly Pro Thr Val Trp Val Lys Asp Gly Thr Gly Leu Val Pro Ser
    50                  55                  60

Glu Arg Val Leu Val Gly Pro Gln Arg Leu Gln Val Leu Asn Ala Ser
65                  70                  75                  80

His Glu Asp Ser Gly Ala Tyr Ser Cys Arg Gln Arg Leu Thr Gln Arg
                85                  90                  95

Val Leu Cys His Phe Ser Val Arg Val Thr Asp Ala Pro Ser Ser Gly
            100                 105                 110

Asp Asp Glu Asp Gly Glu Asp Glu Ala Glu Asp Thr Gly Val Asp Thr
        115                 120                 125

Gly Ala Pro Tyr Trp Thr Arg Pro Glu Arg Met Asp Lys Lys Leu Leu
    130                 135                 140

Ala Val Pro Ala Ala Asn Thr Val Arg Phe Arg Cys Pro Ala Ala Gly
145                 150                 155                 160

Asn Pro Thr Pro Ser Ile Ser Trp Leu Lys Asn Gly Arg Glu Phe Arg
                165                 170                 175

Gly Glu His Arg Ile Gly Gly Ile Lys Leu Arg His Gln Gln Trp Ser
            180                 185                 190

Leu Val Met Glu Ser Val Val Pro Ser Asp Arg Gly Asn Tyr Thr Cys
        195                 200                 205

Val Val Glu Asn Lys Phe Gly Ser Ile Arg Gln Thr Tyr Thr Leu Asp
    210                 215                 220

Val Leu Glu Arg Ser Pro His Arg Pro Ile Leu Gln Ala Gly Leu Pro
225                 230                 235                 240

Ala Asn Gln Thr Ala Val Leu Gly Ser Asp Val Glu Phe His Cys Lys
                245                 250                 255

Val Tyr Ser Asp Ala Gln Pro His Ile Gln Trp Leu Lys His Val Glu
            260                 265                 270

Val Asn Gly Ser Lys Val Gly Pro Asp Gly Thr Pro Tyr Val Thr Val
        275                 280                 285

Leu Lys Ser Trp Ile Ser Glu Ser Val Glu Ala Asp Val Arg Leu Arg
    290                 295                 300

Leu Ala Asn Val Ser Glu Arg Asp Gly Gly Glu Tyr Leu Cys Arg Ala
305                 310                 315                 320
```

Thr Asn Phe Ile Gly Val Ala Glu Lys Ala Phe Trp Leu Ser Val His
                        325                 330                 335

Gly Pro Arg Ala Ala Glu Glu Leu Val Glu Ala Asp Glu Ala Gly
            340                 345                 350

Ser Val Tyr Ala Gly
            355

<210> SEQ ID NO 10
<211> LENGTH: 355
<212> TYPE: PRT
<213> ORGANISM: Homo sapiens
<220> FEATURE:
<223> OTHER INFORMATION: FGFR3, isoform c

<400> SEQUENCE: 10

Ile Ser Glu Ser Leu Gly Thr Glu Gln Arg Val Val Gly Arg Ala Ala
1               5                   10                  15

Glu Val Pro Gly Pro Glu Pro Gly Gln Gln Glu Gln Leu Val Phe Gly
            20                  25                  30

Ser Gly Asp Ala Val Glu Leu Ser Cys Pro Pro Pro Gly Gly Gly Pro
        35                  40                  45

Met Gly Pro Thr Val Trp Val Lys Asp Gly Thr Gly Leu Val Pro Ser
    50                  55                  60

Glu Arg Val Leu Val Gly Pro Gln Arg Leu Gln Val Leu Asn Ala Ser
65                  70                  75                  80

His Glu Asp Ser Gly Ala Tyr Ser Cys Arg Gln Arg Leu Thr Gln Arg
                85                  90                  95

Val Leu Cys His Phe Ser Val Arg Val Thr Asp Ala Pro Ser Ser Gly
            100                 105                 110

Asp Asp Glu Asp Gly Glu Asp Glu Ala Glu Asp Thr Gly Val Asp Thr
        115                 120                 125

Gly Ala Pro Tyr Trp Thr Arg Pro Glu Arg Met Asp Lys Lys Leu Leu
    130                 135                 140

Ala Val Pro Ala Ala Asn Thr Val Arg Phe Arg Cys Pro Ala Ala Gly
145                 150                 155                 160

Asn Pro Thr Pro Ser Ile Ser Trp Leu Lys Asn Gly Arg Glu Phe Arg
                165                 170                 175

Gly Glu His Arg Ile Gly Gly Ile Lys Leu Arg His Gln Gln Trp Ser
            180                 185                 190

Leu Val Met Glu Ser Val Val Pro Ser Asp Arg Gly Asn Tyr Thr Cys
        195                 200                 205

Val Val Glu Asn Lys Phe Gly Ser Ile Arg Gln Thr Tyr Thr Leu Asp
    210                 215                 220

Val Leu Glu Arg Ser Pro His Arg Pro Ile Leu Gln Ala Gly Leu Pro
225                 230                 235                 240

Ala Asn Gln Thr Ala Val Leu Gly Ser Asp Val Glu Phe His Cys Lys
                245                 250                 255

Val Tyr Ser Asp Ala Gln Pro His Ile Gln Trp Leu Lys His Val Glu
            260                 265                 270

Val Asn Gly Ser Lys Val Gly Pro Asp Gly Thr Pro Tyr Val Thr Val
        275                 280                 285

Leu Lys Thr Ala Gly Ala Asn Thr Thr Asp Lys Glu Leu Glu Val Leu
    290                 295                 300

Ser Leu His Asn Val Thr Phe Glu Asp Ala Gly Glu Tyr Thr Cys Leu
305                 310                 315                 320

```
Ala Gly Asn Ser Ile Gly Phe Ser His His Ser Ala Trp Leu Val Val
            325                 330                 335

Leu Pro Ala Glu Glu Leu Val Glu Ala Asp Glu Ala Gly Ser Val
        340                 345                 350

Tyr Ala Gly
        355

<210> SEQ ID NO 11
<211> LENGTH: 63
<212> TYPE: PRT
<213> ORGANISM: Homo sapiens
<220> FEATURE:
<223> OTHER INFORMATION: Fyn kinase SH3 domain

<400> SEQUENCE: 11

Gly Val Thr Leu Phe Val Ala Leu Tyr Asp Tyr Glu Ala Arg Thr Glu
1               5                   10                  15

Asp Asp Leu Ser Phe His Lys Gly Glu Lys Phe Gln Ile Leu Asn Ser
            20                  25                  30

Ser Glu Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60

<210> SEQ ID NO 12
<211> LENGTH: 586
<212> TYPE: PRT
<213> ORGANISM: Artificial Sequence
<220> FEATURE:
<223> OTHER INFORMATION: huFGFR3b-Fc

<400> SEQUENCE: 12

Ile Ser Glu Ser Leu Gly Thr Glu Gln Arg Val Val Gly Arg Ala Ala
1               5                   10                  15

Glu Val Pro Gly Pro Glu Pro Gly Gln Gln Glu Gln Leu Val Phe Gly
            20                  25                  30

Ser Gly Asp Ala Val Glu Leu Ser Cys Pro Pro Pro Gly Gly Gly Pro
        35                  40                  45

Met Gly Pro Thr Val Trp Val Lys Asp Gly Thr Gly Leu Val Pro Ser
    50                  55                  60

Glu Arg Val Leu Val Gly Pro Gln Arg Leu Gln Val Leu Asn Ala Ser
65                  70                  75                  80

His Glu Asp Ser Gly Ala Tyr Ser Cys Arg Gln Arg Leu Thr Gln Arg
                85                  90                  95

Val Leu Cys His Phe Ser Val Arg Val Thr Asp Ala Pro Ser Ser Gly
            100                 105                 110

Asp Asp Glu Asp Gly Glu Asp Glu Ala Glu Asp Thr Gly Val Asp Thr
        115                 120                 125

Gly Ala Pro Tyr Trp Thr Arg Pro Glu Arg Met Asp Lys Lys Leu Leu
    130                 135                 140

Ala Val Pro Ala Ala Asn Thr Val Arg Phe Arg Cys Pro Ala Ala Gly
145                 150                 155                 160

Asn Pro Thr Pro Ser Ile Ser Trp Leu Lys Asn Gly Arg Glu Phe Arg
                165                 170                 175

Gly Glu His Arg Ile Gly Gly Ile Lys Leu Arg His Gln Gln Trp Ser
            180                 185                 190

Leu Val Met Glu Ser Val Val Pro Ser Asp Arg Gly Asn Tyr Thr Cys
        195                 200                 205
```

```
Val Val Glu Asn Lys Phe Gly Ser Ile Arg Gln Thr Tyr Thr Leu Asp
    210                 215                 220

Val Leu Glu Arg Ser Pro His Arg Pro Ile Leu Gln Ala Gly Leu Pro
225                 230                 235                 240

Ala Asn Gln Thr Ala Val Leu Gly Ser Asp Val Glu Phe His Cys Lys
                245                 250                 255

Val Tyr Ser Asp Ala Gln Pro His Ile Gln Trp Leu Lys His Val Glu
            260                 265                 270

Val Asn Gly Ser Lys Val Gly Pro Asp Gly Thr Pro Tyr Val Thr Val
        275                 280                 285

Leu Lys Ser Trp Ile Ser Glu Ser Val Glu Ala Asp Val Arg Leu Arg
    290                 295                 300

Leu Ala Asn Val Ser Glu Arg Asp Gly Gly Glu Tyr Leu Cys Arg Ala
305                 310                 315                 320

Thr Asn Phe Ile Gly Val Ala Glu Lys Ala Phe Trp Leu Ser Val His
                325                 330                 335

Gly Pro Arg Ala Ala Glu Glu Leu Val Glu Ala Asp Glu Ala Gly
            340                 345                 350

Ser Val Tyr Ala Gly Arg Ser Asp Lys Thr His Thr Cys Pro Pro Cys
        355                 360                 365

Pro Ala Pro Glu Leu Leu Gly Gly Pro Ser Val Phe Leu Phe Pro Pro
370                 375                 380

Lys Pro Lys Asp Thr Leu Met Ile Ser Arg Thr Pro Glu Val Thr Cys
385                 390                 395                 400

Val Val Val Asp Val Ser His Glu Asp Pro Glu Val Lys Phe Asn Trp
                405                 410                 415

Tyr Val Asp Gly Val Glu Val His Asn Ala Lys Thr Lys Pro Arg Glu
            420                 425                 430

Glu Gln Tyr Asn Ser Thr Tyr Arg Val Val Ser Val Leu Thr Val Leu
        435                 440                 445

His Gln Asp Trp Leu Asn Gly Lys Glu Tyr Lys Cys Lys Val Ser Asn
    450                 455                 460

Lys Ala Leu Pro Ala Pro Ile Glu Lys Thr Ile Ser Lys Ala Lys Gly
465                 470                 475                 480

Gln Pro Arg Glu Pro Gln Val Tyr Thr Leu Pro Pro Ser Arg Glu Glu
                485                 490                 495

Met Thr Lys Asn Gln Val Ser Leu Thr Cys Leu Val Lys Gly Phe Tyr
            500                 505                 510

Pro Ser Asp Ile Ala Val Glu Trp Glu Ser Asn Gly Gln Pro Glu Asn
        515                 520                 525

Asn Tyr Lys Thr Thr Pro Pro Val Leu Asp Ser Asp Gly Ser Phe Phe
    530                 535                 540

Leu Tyr Ser Lys Leu Thr Val Asp Lys Ser Arg Trp Gln Gln Gly Asn
545                 550                 555                 560

Val Phe Ser Cys Ser Val Met His Glu Ala Leu His Asn His Tyr Thr
                565                 570                 575

Gln Lys Ser Leu Ser Leu Ser Pro Gly Lys
            580                 585

<210> SEQ ID NO 13
<211> LENGTH: 584
<212> TYPE: PRT
<213> ORGANISM: Artificial Sequence
<220> FEATURE:
```

<223> OTHER INFORMATION: huFGFR3c-Fc

<400> SEQUENCE: 13

```
Ile Ser Glu Ser Leu Gly Thr Glu Gln Arg Val Val Gly Arg Ala Ala
  1               5                  10                  15
Glu Val Pro Gly Pro Glu Pro Gly Gln Gln Glu Gln Leu Val Phe Gly
                 20                  25                  30
Ser Gly Asp Ala Val Glu Leu Ser Cys Pro Pro Pro Gly Gly Gly Pro
             35                  40                  45
Met Gly Pro Thr Val Trp Val Lys Asp Gly Thr Gly Leu Val Pro Ser
 50                  55                  60
Glu Arg Val Leu Val Gly Pro Gln Arg Leu Gln Val Leu Asn Ala Ser
 65                  70                  75                  80
His Glu Asp Ser Gly Ala Tyr Ser Cys Arg Gln Arg Leu Thr Gln Arg
                 85                  90                  95
Val Leu Cys His Phe Ser Val Arg Val Thr Asp Ala Pro Ser Ser Gly
            100                 105                 110
Asp Asp Glu Asp Gly Glu Asp Glu Ala Glu Asp Thr Gly Val Asp Thr
            115                 120                 125
Gly Ala Pro Tyr Trp Thr Arg Pro Glu Arg Met Asp Lys Lys Leu Leu
130                 135                 140
Ala Val Pro Ala Ala Asn Thr Val Arg Phe Arg Cys Pro Ala Ala Gly
145                 150                 155                 160
Asn Pro Thr Pro Ser Ile Ser Trp Leu Lys Asn Gly Arg Glu Phe Arg
                165                 170                 175
Gly Glu His Arg Ile Gly Gly Ile Lys Leu Arg His Gln Gln Trp Ser
            180                 185                 190
Leu Val Met Glu Ser Val Val Pro Ser Asp Arg Gly Asn Tyr Thr Cys
        195                 200                 205
Val Val Glu Asn Lys Phe Gly Ser Ile Arg Gln Thr Tyr Thr Leu Asp
    210                 215                 220
Val Leu Glu Arg Ser Pro His Arg Pro Ile Leu Gln Ala Gly Leu Pro
225                 230                 235                 240
Ala Asn Gln Thr Ala Val Leu Gly Ser Asp Val Glu Phe His Cys Lys
                245                 250                 255
Val Tyr Ser Asp Ala Gln Pro His Ile Gln Trp Leu Lys His Val Glu
            260                 265                 270
Val Asn Gly Ser Lys Val Gly Pro Asp Gly Thr Pro Tyr Val Thr Val
        275                 280                 285
Leu Lys Thr Ala Gly Ala Asn Thr Thr Asp Lys Glu Leu Glu Val Leu
    290                 295                 300
Ser Leu His Asn Val Thr Phe Glu Asp Ala Gly Glu Tyr Thr Cys Leu
305                 310                 315                 320
Ala Gly Asn Ser Ile Gly Phe Ser His His Ser Ala Trp Leu Val Val
                325                 330                 335
Leu Pro Ala Glu Glu Leu Val Glu Ala Asp Glu Ala Gly Ser Val
            340                 345                 350
Tyr Ala Gly Arg Ser Asp Lys Thr His Thr Cys Pro Pro Cys Pro Ala
        355                 360                 365
Pro Glu Leu Leu Gly Gly Pro Ser Val Phe Leu Phe Pro Pro Lys Pro
    370                 375                 380
Lys Asp Thr Leu Met Ile Ser Arg Thr Pro Glu Val Thr Cys Val Val
385                 390                 395                 400
```

```
Val Asp Val Ser His Glu Asp Pro Glu Val Lys Phe Asn Trp Tyr Val
            405                 410                 415

Asp Gly Val Glu Val His Asn Ala Lys Thr Lys Pro Arg Glu Glu Gln
            420                 425                 430

Tyr Asn Ser Thr Tyr Arg Val Val Ser Val Leu Thr Val Leu His Gln
            435                 440                 445

Asp Trp Leu Asn Gly Lys Glu Tyr Lys Cys Lys Val Ser Asn Lys Ala
        450                 455                 460

Leu Pro Ala Pro Ile Glu Lys Thr Ile Ser Lys Ala Lys Gly Gln Pro
465                 470                 475                 480

Arg Glu Pro Gln Val Tyr Thr Leu Pro Pro Ser Arg Glu Glu Met Thr
                485                 490                 495

Lys Asn Gln Val Ser Leu Thr Cys Leu Val Lys Gly Phe Tyr Pro Ser
                500                 505                 510

Asp Ile Ala Val Glu Trp Glu Ser Asn Gly Gln Pro Glu Asn Asn Tyr
            515                 520                 525

Lys Thr Thr Pro Pro Val Leu Asp Ser Asp Gly Ser Phe Phe Leu Tyr
        530                 535                 540

Ser Lys Leu Thr Val Asp Lys Ser Arg Trp Gln Gln Gly Asn Val Phe
545                 550                 555                 560

Ser Cys Ser Val Met His Glu Ala Leu His Asn His Tyr Thr Gln Lys
                565                 570                 575

Ser Leu Ser Leu Ser Pro Gly Lys
            580

<210> SEQ ID NO 14
<211> LENGTH: 583
<212> TYPE: PRT
<213> ORGANISM: Artificial Sequence
<220> FEATURE:
<223> OTHER INFORMATION: cyFGFR3c-Fc

<400> SEQUENCE: 14

Ser Glu Ser Leu Gly Thr Glu Gln Arg Val Val Gly Arg Val Ala Glu
1               5                   10                  15

Val Ser Gly Pro Glu Pro Ser Gln Gln Glu Gln Leu Val Phe Gly Ser
            20                  25                  30

Gly Asp Ala Val Glu Leu Ser Cys Pro Pro Gly Gly Gly Pro Met
            35                  40                  45

Gly Pro Thr Val Trp Val Lys Asp Gly Ala Gly Leu Val Pro Ser Glu
        50                  55                  60

Arg Val Leu Val Gly Pro Gln Arg Leu Gln Val Leu Asn Ala Ser His
65                  70                  75                  80

Glu Asp Ser Gly Ala Tyr Ser Cys Arg Gln Arg Leu Thr Gln Leu Val
                85                  90                  95

Leu Cys His Phe Ser Val Arg Val Thr Asp Ala Pro Ser Ser Gly Asp
            100                 105                 110

Asp Glu Asp Gly Glu Asp Glu Ala Glu Asp Thr Gly Val Asp Thr Gly
            115                 120                 125

Ala Pro Tyr Trp Thr Arg Pro Glu Arg Met Asp Lys Lys Leu Leu Ala
        130                 135                 140

Val Pro Ala Ala Asn Thr Val Arg Phe Arg Cys Pro Ala Ala Gly Asn
145                 150                 155                 160

Pro Thr Pro Ser Ile Ser Trp Leu Lys Asn Gly Lys Glu Phe Arg Gly
                165                 170                 175
```

-continued

Glu His Arg Ile Gly Gly Ile Lys Leu Arg His Gln Gln Trp Ser Leu
            180                 185                 190

Val Met Glu Ser Val Val Pro Ser Asp Arg Gly Asn Tyr Thr Cys Val
        195                 200                 205

Val Glu Asn Lys Phe Gly Ser Ile Arg Gln Thr Tyr Thr Leu Asp Val
    210                 215                 220

Leu Glu Arg Ser Pro His Arg Pro Ile Leu Gln Ala Gly Leu Pro Ala
225                 230                 235                 240

Asn Gln Thr Ala Val Leu Gly Ser Asp Val Glu Phe His Cys Lys Val
                245                 250                 255

Tyr Ser Asp Ala Gln Pro His Ile Gln Trp Leu Lys His Val Glu Val
            260                 265                 270

Asn Gly Ser Lys Val Gly Pro Asp Gly Thr Pro Tyr Val Thr Val Leu
        275                 280                 285

Lys Thr Ala Gly Ala Asn Thr Thr Asp Lys Glu Leu Glu Val Leu Ser
    290                 295                 300

Leu His Asn Val Thr Phe Glu Asp Ala Gly Glu Tyr Thr Cys Leu Ala
305                 310                 315                 320

Gly Asn Ser Ile Gly Phe Ser His His Ser Ala Trp Leu Val Val Leu
                325                 330                 335

Pro Ala Glu Glu Glu Leu Val Glu Ala Asp Glu Ala Gly Ser Val Tyr
            340                 345                 350

Ala Gly Arg Ser Asp Lys Thr His Thr Cys Pro Pro Cys Pro Ala Pro
        355                 360                 365

Glu Leu Leu Gly Gly Pro Ser Val Phe Leu Phe Pro Pro Lys Pro Lys
    370                 375                 380

Asp Thr Leu Met Ile Ser Arg Thr Pro Glu Val Thr Cys Val Val Val
385                 390                 395                 400

Asp Val Ser His Glu Asp Pro Glu Val Lys Phe Asn Trp Tyr Val Asp
                405                 410                 415

Gly Val Glu Val His Asn Ala Lys Thr Lys Pro Arg Glu Glu Gln Tyr
            420                 425                 430

Asn Ser Thr Tyr Arg Val Val Ser Val Leu Thr Val Leu His Gln Asp
        435                 440                 445

Trp Leu Asn Gly Lys Glu Tyr Lys Cys Lys Val Ser Asn Lys Ala Leu
    450                 455                 460

Pro Ala Pro Ile Glu Lys Thr Ile Ser Lys Ala Lys Gly Gln Pro Arg
465                 470                 475                 480

Glu Pro Gln Val Tyr Thr Leu Pro Pro Ser Arg Glu Glu Met Thr Lys
                485                 490                 495

Asn Gln Val Ser Leu Thr Cys Leu Val Lys Gly Phe Tyr Pro Ser Asp
            500                 505                 510

Ile Ala Val Glu Trp Glu Ser Asn Gly Gln Pro Glu Asn Asn Tyr Lys
        515                 520                 525

Thr Thr Pro Pro Val Leu Asp Ser Asp Gly Ser Phe Phe Leu Tyr Ser
    530                 535                 540

Lys Leu Thr Val Asp Lys Ser Arg Trp Gln Gln Gly Asn Val Phe Ser
545                 550                 555                 560

Cys Ser Val Met His Glu Ala Leu His Asn His Tyr Thr Gln Lys Ser
                565                 570                 575

Leu Ser Leu Ser Pro Gly Lys
            580

<210> SEQ ID NO 15
<211> LENGTH: 347
<212> TYPE: PRT
<213> ORGANISM: Artificial Sequence
<220> FEATURE:
<223> OTHER INFORMATION: muFGFR3c-His

<400> SEQUENCE: 15

| Ala | Ala | Glu | Val | Pro | Gly | Pro | Glu | Pro | Ser | Gln | Gln | Glu | Gln | Val | Ala |
|---|---|---|---|---|---|---|---|---|---|---|---|---|---|---|---|
| 1 | | | | 5 | | | | | 10 | | | | | 15 | |

| Phe | Gly | Ser | Gly | Asp | Thr | Val | Glu | Leu | Ser | Cys | His | Pro | Pro | Gly | Gly |
| | | | 20 | | | | | 25 | | | | | 30 | | |

| Ala | Pro | Thr | Gly | Pro | Thr | Val | Trp | Ala | Lys | Asp | Gly | Thr | Gly | Leu | Val |
| | | 35 | | | | | 40 | | | | | 45 | | | |

| Ala | Ser | His | Arg | Ile | Leu | Val | Gly | Pro | Gln | Arg | Leu | Gln | Val | Leu | Asn |
| | 50 | | | | | 55 | | | | | 60 | | | | |

| Ala | Ser | His | Glu | Asp | Ala | Gly | Val | Tyr | Ser | Cys | Gln | His | Arg | Leu | Thr |
| 65 | | | | | 70 | | | | | 75 | | | | | 80 |

| Arg | Arg | Val | Leu | Cys | His | Phe | Ser | Val | Arg | Val | Thr | Asp | Ala | Pro | Ser |
| | | | | 85 | | | | | 90 | | | | | 95 | |

| Ser | Gly | Asp | Asp | Glu | Asp | Gly | Glu | Asp | Val | Ala | Glu | Asp | Thr | Gly | Ala |
| | | | 100 | | | | | 105 | | | | | 110 | | |

| Pro | Tyr | Trp | Thr | Arg | Pro | Glu | Arg | Met | Asp | Lys | Lys | Leu | Leu | Ala | Val |
| | | 115 | | | | | 120 | | | | | 125 | | | |

| Pro | Ala | Ala | Asn | Thr | Val | Arg | Phe | Arg | Cys | Pro | Ala | Ala | Gly | Asn | Pro |
| | 130 | | | | | 135 | | | | | 140 | | | | |

| Thr | Pro | Ser | Ile | Ser | Trp | Leu | Lys | Asn | Gly | Lys | Glu | Phe | Arg | Gly | Glu |
| 145 | | | | | 150 | | | | | 155 | | | | | 160 |

| His | Arg | Ile | Gly | Gly | Ile | Lys | Leu | Arg | His | Gln | Gln | Trp | Ser | Leu | Val |
| | | | | 165 | | | | | 170 | | | | | 175 | |

| Met | Glu | Ser | Val | Val | Pro | Ser | Asp | Arg | Gly | Asn | Tyr | Thr | Cys | Val | Val |
| | | | 180 | | | | | 185 | | | | | 190 | | |

| Glu | Asn | Lys | Phe | Gly | Ser | Ile | Arg | Gln | Thr | Tyr | Thr | Leu | Asp | Val | Leu |
| | | 195 | | | | | 200 | | | | | 205 | | | |

| Glu | Arg | Ser | Pro | His | Arg | Pro | Ile | Leu | Gln | Ala | Gly | Leu | Pro | Ala | Asn |
| | 210 | | | | | 215 | | | | | 220 | | | | |

| Gln | Thr | Ala | Ile | Leu | Gly | Ser | Asp | Val | Glu | Phe | His | Cys | Lys | Val | Tyr |
| 225 | | | | | 230 | | | | | 235 | | | | | 240 |

| Ser | Asp | Ala | Gln | Pro | His | Ile | Gln | Trp | Leu | Lys | His | Val | Glu | Val | Asn |
| | | | | 245 | | | | | 250 | | | | | 255 | |

| Gly | Ser | Lys | Val | Gly | Pro | Asp | Gly | Thr | Pro | Tyr | Val | Thr | Val | Leu | Lys |
| | | | 260 | | | | | 265 | | | | | 270 | | |

| Thr | Ala | Gly | Ala | Asn | Thr | Thr | Asp | Lys | Glu | Leu | Glu | Val | Leu | Ser | Leu |
| | | 275 | | | | | 280 | | | | | 285 | | | |

| His | Asn | Val | Thr | Phe | Glu | Asp | Ala | Gly | Glu | Tyr | Thr | Cys | Leu | Ala | Gly |
| | 290 | | | | | 295 | | | | | 300 | | | | |

| Asn | Ser | Ile | Gly | Phe | Ser | His | His | Ser | Ala | Trp | Leu | Val | Val | Leu | Pro |
| 305 | | | | | 310 | | | | | 315 | | | | | 320 |

| Ala | Glu | Glu | Glu | Leu | Met | Glu | Thr | Asp | Glu | Ala | Gly | Ser | Val | Tyr | Ala |
| | | | | 325 | | | | | 330 | | | | | 335 | |

| Gly | His | His | His | His | His | His | His | His |
| | | | 340 | | | | | 345 |

<210> SEQ ID NO 16
<211> LENGTH: 361
<212> TYPE: PRT

<213> ORGANISM: Artificial Sequence
<220> FEATURE:
<223> OTHER INFORMATION: huD1-Fc

<400> SEQUENCE: 16

```
Ser Glu Ser Leu Gly Thr Glu Gln Arg Val Val Gly Arg Ala Ala Glu
1               5                   10                  15

Val Pro Gly Pro Glu Pro Gly Gln Gln Glu Gln Leu Val Phe Gly Ser
            20                  25                  30

Gly Asp Ala Val Glu Leu Ser Cys Pro Pro Gly Gly Pro Met
        35                  40                  45

Gly Pro Thr Val Trp Val Lys Asp Gly Thr Gly Leu Val Pro Ser Glu
    50                  55                  60

Arg Val Leu Val Gly Pro Gln Arg Leu Gln Val Leu Asn Ala Ser His
65                  70                  75                  80

Glu Asp Ser Gly Ala Tyr Ser Cys Arg Gln Arg Leu Thr Gln Arg Val
                85                  90                  95

Leu Cys His Phe Ser Val Arg Val Thr Asp Ala Pro Ser Ser Gly Asp
            100                 105                 110

Asp Glu Asp Gly Glu Asp Glu Ala Glu Asp Thr Gly Val Asp Thr Gly
        115                 120                 125

Ala Gly Gly Gly Ser Asp Lys Thr His Thr Cys Pro Pro Cys Pro
    130                 135                 140

Ala Pro Glu Leu Leu Gly Gly Pro Ser Val Phe Leu Phe Pro Pro Lys
145                 150                 155                 160

Pro Lys Asp Thr Leu Met Ile Ser Arg Thr Pro Glu Val Thr Cys Val
                165                 170                 175

Val Val Asp Val Ser His Glu Asp Pro Glu Val Lys Phe Asn Trp Tyr
            180                 185                 190

Val Asp Gly Val Glu Val His Asn Ala Lys Thr Lys Pro Arg Glu Glu
        195                 200                 205

Gln Tyr Asn Ser Thr Tyr Arg Val Val Ser Val Leu Thr Val Leu His
    210                 215                 220

Gln Asp Trp Leu Asn Gly Lys Glu Tyr Lys Cys Lys Val Ser Asn Lys
225                 230                 235                 240

Ala Leu Pro Ala Pro Ile Glu Lys Thr Ile Ser Lys Ala Lys Gly Gln
                245                 250                 255

Pro Arg Glu Pro Gln Val Tyr Thr Leu Pro Pro Ser Arg Glu Glu Met
            260                 265                 270

Thr Lys Asn Gln Val Ser Leu Thr Cys Leu Val Lys Gly Phe Tyr Pro
        275                 280                 285

Ser Asp Ile Ala Val Glu Trp Glu Ser Asn Gly Gln Pro Glu Asn Asn
    290                 295                 300

Tyr Lys Thr Thr Pro Pro Val Leu Asp Ser Asp Gly Ser Phe Phe Leu
305                 310                 315                 320

Tyr Ser Lys Leu Thr Val Asp Lys Ser Arg Trp Gln Gln Gly Asn Val
                325                 330                 335

Phe Ser Cys Ser Val Met His Glu Ala Leu His Asn His Tyr Thr Gln
            340                 345                 350

Lys Ser Leu Ser Leu Ser Pro Gly Lys
        355                 360
```

<210> SEQ ID NO 17
<211> LENGTH: 340
<212> TYPE: PRT

<213> ORGANISM: Artificial Sequence
<220> FEATURE:
<223> OTHER INFORMATION: huD2-Fc

<400> SEQUENCE: 17

```
Ala Pro Tyr Trp Thr Arg Pro Glu Arg Met Asp Lys Lys Leu Leu Ala
1               5                   10                  15

Val Pro Ala Ala Asn Thr Val Arg Phe Arg Cys Pro Ala Ala Gly Asn
            20                  25                  30

Pro Thr Pro Ser Ile Ser Trp Leu Lys Asn Gly Arg Glu Phe Arg Gly
        35                  40                  45

Glu His Arg Ile Gly Gly Ile Lys Leu Arg His Gln Gln Trp Ser Leu
    50                  55                  60

Val Met Glu Ser Val Val Pro Ser Asp Arg Gly Asn Tyr Thr Cys Val
65                  70                  75                  80

Val Glu Asn Lys Phe Gly Ser Ile Arg Gln Thr Tyr Thr Leu Asp Val
                85                  90                  95

Leu Glu Gly Gly Gly Gly Ser Gly Gly Gly Ser Gly Gly Gly Gly
            100                 105                 110

Ser Asp Lys Thr His Thr Cys Pro Pro Cys Pro Ala Pro Glu Leu Leu
            115                 120                 125

Gly Gly Pro Ser Val Phe Leu Phe Pro Pro Lys Pro Lys Asp Thr Leu
        130                 135                 140

Met Ile Ser Arg Thr Pro Glu Val Thr Cys Val Val Val Asp Val Ser
145                 150                 155                 160

His Glu Asp Pro Glu Val Lys Phe Asn Trp Tyr Val Asp Gly Val Glu
                165                 170                 175

Val His Asn Ala Lys Thr Lys Pro Arg Glu Glu Gln Tyr Asn Ser Thr
            180                 185                 190

Tyr Arg Val Val Ser Val Leu Thr Val Leu His Gln Asp Trp Leu Asn
        195                 200                 205

Gly Lys Glu Tyr Lys Cys Lys Val Ser Asn Lys Ala Leu Pro Ala Pro
    210                 215                 220

Ile Glu Lys Thr Ile Ser Lys Ala Lys Gly Gln Pro Arg Glu Pro Gln
225                 230                 235                 240

Val Tyr Thr Leu Pro Pro Ser Arg Glu Glu Met Thr Lys Asn Gln Val
                245                 250                 255

Ser Leu Thr Cys Leu Val Lys Gly Phe Tyr Pro Ser Asp Ile Ala Val
            260                 265                 270

Glu Trp Glu Ser Asn Gly Gln Pro Glu Asn Asn Tyr Lys Thr Thr Pro
        275                 280                 285

Pro Val Leu Asp Ser Asp Gly Ser Phe Phe Leu Tyr Ser Lys Leu Thr
    290                 295                 300

Val Asp Lys Ser Arg Trp Gln Gln Gly Asn Val Phe Ser Cys Ser Val
305                 310                 315                 320

Met His Glu Ala Leu His Asn His Tyr Thr Gln Lys Ser Leu Ser Leu
                325                 330                 335

Ser Pro Gly Lys
            340
```

<210> SEQ ID NO 18
<211> LENGTH: 468
<212> TYPE: PRT
<213> ORGANISM: Artificial Sequence
<220> FEATURE:
<223> OTHER INFORMATION: huD1-D2-Fc

<400> SEQUENCE: 18

```
Ser Glu Ser Leu Gly Thr Glu Gln Arg Val Val Gly Arg Ala Ala Glu
1               5                   10                  15

Val Pro Gly Pro Glu Pro Gly Gln Gln Glu Gln Leu Val Phe Gly Ser
            20                  25                  30

Gly Asp Ala Val Glu Leu Ser Cys Pro Pro Gly Gly Gly Pro Met
            35                  40                  45

Gly Pro Thr Val Trp Val Lys Asp Gly Thr Gly Leu Val Pro Ser Glu
50                  55                  60

Arg Val Leu Val Gly Pro Gln Arg Leu Gln Val Leu Asn Ala Ser His
65                  70                  75                  80

Glu Asp Ser Gly Ala Tyr Ser Cys Arg Gln Arg Leu Thr Gln Arg Val
                85                  90                  95

Leu Cys His Phe Ser Val Arg Val Thr Asp Ala Pro Ser Ser Gly Asp
            100                 105                 110

Asp Glu Asp Gly Glu Asp Glu Ala Glu Asp Thr Gly Val Asp Thr Gly
            115                 120                 125

Ala Pro Tyr Trp Thr Arg Pro Glu Arg Met Asp Lys Lys Leu Leu Ala
130                 135                 140

Val Pro Ala Ala Asn Thr Val Arg Phe Arg Cys Pro Ala Ala Gly Asn
145                 150                 155                 160

Pro Thr Pro Ser Ile Ser Trp Leu Lys Asn Gly Arg Glu Phe Arg Gly
                165                 170                 175

Glu His Arg Ile Gly Gly Ile Lys Leu Arg His Gln Gln Trp Ser Leu
            180                 185                 190

Val Met Glu Ser Val Val Pro Ser Asp Arg Gly Asn Tyr Thr Cys Val
            195                 200                 205

Val Glu Asn Lys Phe Gly Ser Ile Arg Gln Thr Tyr Thr Leu Asp Val
210                 215                 220

Leu Glu Gly Gly Gly Ser Gly Gly Gly Ser Gly Gly Gly Gly
225                 230                 235                 240

Ser Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
            275                 280                 285

His Glu Asp Pro Glu Val Lys Phe Asn Trp Tyr Val Asp Gly Val Glu
290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
            355                 360                 365

Val Tyr Thr Leu Pro Pro Ser Arg Glu Glu Met Thr Lys Asn Gln Val
370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
```

```
                405                 410                 415
Pro Val Leu Asp Ser Asp Gly Ser Phe Phe Leu Tyr Ser Lys Leu Thr
        420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys
465

<210> SEQ ID NO 19
<211> LENGTH: 64
<212> TYPE: PRT
<213> ORGANISM: Artificial Sequence
<220> FEATURE:
<223> OTHER INFORMATION: Consensus sequence anti-FGFR3 Fynomers
<220> FEATURE:
<221> NAME/KEY: VARIANT
<222> LOCATION: 51
<223> OTHER INFORMATION: any amino acid

<400> SEQUENCE: 19

Gly Val Thr Leu Phe Val Ala Leu Tyr Asp Tyr Glu Val Met Ser Thr
1               5                   10                  15

Thr Ala Leu Ser Phe His Lys Gly Glu Lys Phe Gln Ile Leu Ser Gln
            20                  25                  30

Ser Pro His Gly Gln Tyr Trp Glu Ala Arg Ser Leu Thr Thr Gly Glu
        35                  40                  45

Thr Gly Xaa Ile Pro Ser Asn Tyr Val Ala Pro Val Asp Ser Ile Gln
    50                  55                  60

<210> SEQ ID NO 20
<211> LENGTH: 7
<212> TYPE: PRT
<213> ORGANISM: Artificial Sequence
<220> FEATURE:
<223> OTHER INFORMATION: RT-loop sequence

<400> SEQUENCE: 20

Glu Val Met Ser Thr Thr Ala
1               5

<210> SEQ ID NO 21
<211> LENGTH: 5
<212> TYPE: PRT
<213> ORGANISM: Artificial Sequence
<220> FEATURE:
<223> OTHER INFORMATION: src-loop sequence

<400> SEQUENCE: 21

Ser Gln Ser Pro His
1               5

<210> SEQ ID NO 22
<211> LENGTH: 64
<212> TYPE: PRT
<213> ORGANISM: Artificial Sequence
<220> FEATURE:
<223> OTHER INFORMATION: FF40L54A5 anti-FGFR3 Fynomer

<400> SEQUENCE: 22

Gly Val Thr Leu Phe Val Ala Leu Tyr Asp Tyr Glu Val Met Ser Thr
1               5                   10                  15
```

-continued

```
Thr Ala Leu Ser Phe His Lys Gly Glu Lys Phe Gln Ile Leu Ser Gln
            20                  25                  30

Ser Pro His Gly Gln Tyr Trp Glu Ala Arg Ser Leu Thr Gly Glu
            35                  40                  45

Thr Gly Trp Ile Pro Ser Asn Tyr Val Ala Pro Val Asp Ser Ile Gln
            50                  55                  60
```